(12) United States Patent
Kuhnke et al.

(10) Patent No.: US 8,207,150 B2
(45) Date of Patent: *Jun. 26, 2012

(54) 17β-CYANO-19-NOR-ANDROST-4-ENE DERIVATIVE, ITS USE AND MEDICAMENTS COMPRISING THE DERIVATIVE

(75) Inventors: Joachim Kuhnke, Potsdam (DE); Jan Huebner, Berlin (DE); Rolf Bohlmann, Berlin (DE); Thomas Frenzel, Hofheim (DE); Ulrich Klar, Berlin (DE); Frederik Menges, Schriesheim (DE); Sven Ring, Jena (DE); Steffen Borden, Berlin (DE); Hans-Peter Muhn, Berlin (DE); Katja Prelle, Berlin, DE (US)

(73) Assignee: Bayer Pharma AG, Berlin (DE)

( * ) Notice: Subject to any disclaimer, the term of this patent is extended or adjusted under 35 U.S.C. 154(b) by 822 days.

This patent is subject to a terminal disclaimer.

(21) Appl. No.: 12/137,111

(22) Filed: Jun. 11, 2008

(65) Prior Publication Data

US 2009/0048217 A1    Feb. 19, 2009

Related U.S. Application Data

(60) Provisional application No. 60/943,617, filed on Jun. 13, 2007.

(30) Foreign Application Priority Data

Jun. 12, 2007 (DE) .................... 10 2007 027 637

(51) Int. Cl.
*A61K 31/56* (2006.01)
*C07J 3/00* (2006.01)

(52) U.S. Cl. ........................ 514/177; 552/611

(58) Field of Classification Search .................. 552/646, 552/647, 648, 611; 514/177, 178
See application file for complete search history.

(56) References Cited

U.S. PATENT DOCUMENTS

| | | | |
|---|---|---|---|
| 3,043,833 A | 7/1962 | Pietro De Ruggieri | |
| 3,400,136 A | 9/1968 | Holden et al. | |
| 3,463,776 A | 8/1969 | Lester et al. | |
| 3,705,179 A * | 12/1972 | Marhall et al. | 552/6 |
| 3,770,725 A * | 11/1973 | Gasc et al. | 540/36 |
| 4,252,800 A * | 2/1981 | Blye et al. | 514/178 |
| 4,544,554 A * | 10/1985 | Pasquale | 514/170 |
| RE37,838 E * | 9/2002 | Spona et al. | 514/170 |
| 2009/0048217 A1 | 2/2009 | Kuhnke et al. | |

FOREIGN PATENT DOCUMENTS

| | | |
|---|---|---|
| DE | 2226552 | 1/1973 |
| EP | 0785211 A1 | 7/1997 |
| GB | 1308849 | 3/1973 |
| WO | 8500609 A1 | 2/1985 |
| WO | WO 2008151746 R | 1/2009 |

OTHER PUBLICATIONS

Souillac, et al., Characterization of Delivery Systems, Differential Scanning Calorimetry, pp. 217-218 (in Encyclopedia of Controlled Drug Delivery, 1999, John Wiley & Sons, pp. 212-227).*

Vippagunta et al. (Advanced Drug Delivery Reviews, 48 (2001), pp. 3-26).*
Wilks, John et al. "Steroid Binding Specificity of the Hamster Uterine Progesterone Receptor." Steroids vol. 35 No. 6 (Jun. 1980): 697-706.
Dore, Jean-Christophe et al. "Correspondence Analysis Applied to Steroid Receptor Binding." Journal of Medicinal Chemistry 29 (1986): 54-60.
Salman, Mohammad and Gary C. Chamness. "A Potential Radioiodinated Ligand for Androgen Receptor: 7alpha-Methyl-17alpha-(2'-(E)-iodovinyl)-19-nortestosterone." Journal of Medicinal Chemistry 34 (1991): 1019-1024.
De Gooyer, Marcel E., et al. "Receptor Profiling and Endocrine Interactions of Tibolone." Steroids 68 (2003): 21-30.

* cited by examiner

*Primary Examiner* — Barbara P Badio
(74) *Attorney, Agent, or Firm* — Millen, White, Zelano & Branigan, P.C.

(57) ABSTRACT

The 17β-cyano-19-nor-androst-4-ene derivatives of the present invention possess gestagenic activity. They have the general chemical formula 1, in which Z is selected from the group comprising O, two hydrogen atoms, NOR and NNHSO$_2$R, in which R is hydrogen or $C_1$-$C_4$-alkyl, $R^4$ is hydrogen or halogen, furthermore either: $R^{6a}$, $R^{6b}$ together form methylene or 1,2-ethanediyl or $R^{6a}$ is hydrogen and $R^{6b}$ is selected from the group comprising hydrogen, methyl and hydroxymethylene, and $R^7$ is selected from the group comprising hydrogen, $C_1$-$C_4$-alkyl, $C_2$-$C_3$-alkenyl and cyclopropyl, or: $R^{6a}$ is hydrogen and $R^{6b}$ and $R^7$ together form methylene or are omitted with formation of a double bond between $C^6$ and $C^7$, $R^9$, $R^{10}$ are hydrogen or are omitted with formation of a double bond between $C^9$ and $C^{10}$, $R^{15}$, $R^{16}$ are hydrogen or together form methylene, $R^{17}$ is selected from the group comprising hydrogen, $C_1$-$C_4$-alkyl and allyl, where at least one of the substituents $R^4$, $R^{6a}$, $R^{6b}$, $R^7$, $R^{15}$, $R^{16}$ and $R^{17}$ is unequal to hydrogen or $R^{6b}$ and $R^7$ are omitted with formation of a double bond between $C^6$ and $C^7$, and moreover comprise their solvates, hydrates, stereoisomers, diastereomers, enantiomers and salts.

(1)

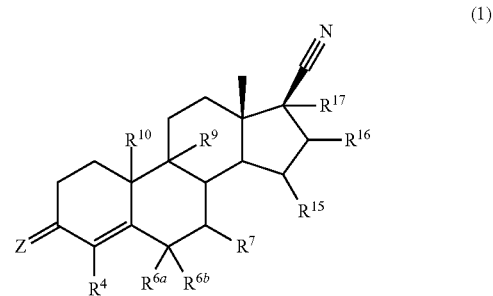

10 Claims, No Drawings

17β-CYANO-19-NOR-ANDROST-4-ENE DERIVATIVE, ITS USE AND MEDICAMENTS COMPRISING THE DERIVATIVE

This application claims the benefit of the filing date of U.S. Provisional Application Ser. No. 60/943,617 filed Jun. 13, 2007.

DESCRIPTION

The invention relates to certain 17β-cyano-19-nor-androst-4-ene derivatives, their use and to medicaments comprising the derivatives and having gestagenic action, for example for the treatment of pre-, peri- and postmenopausal symptoms and of premenstrual symptoms.

From the literature, compounds having gestagenic, antimineralcorticoid, antian-drogenic oder antioestrogenic action based on a steroid structure are known, which are derived, for example, from 19-nor-androst-4-en-3-one or a derivative thereof (the numbering of the steroid structure can be taken, for example, from Fresenius/Görlitzer 3rd ed. 1991 "Organisch-chemische Nomenklatur" [Organic chemical nomenclature] pp. 60 ff.).

Thus, WO 2006072467 A1 describes the compound 6β,7β-15β,16β-dimethylene-3-oxo-17-pregn-4-ene-21,17β-carbolactone (drospirenone) having gestagenic action, which has been used, for example, in an oral contraceptive and a preparation for the treatment of postmenopausal symptoms. On account of its comparatively low affinity for the gestagen receptor and its comparatively high ovulation-inhibiting dose, drospirenone is contained in the contraceptive, however, in the relatively high daily dose of 3 mg. Drospirenone is moreover distinguished in that, in addition to the gestagenic action, it has aldosterone-antagonistic (antimineralcorticoid) and antiandrogenic action. These two properties make drospirenone very similar in its pharmacological profile to the natural gestagen progesterone which, however, unlike drospirenone is not adequately bioavailable orally. In order to lower the dose to be administered, in WO 2006072467 A1 an 18-methyl-19-nor-17-pregn-4-ene-21,17-carbolactone and pharmaceutical preparations comprising this are further proposed which have a higher gestagenic potency than drospirenone.

In addition, for example, U.S. Pat. No. 3,705,179 discloses steroids which have antiandrogenic activity and are suitable for the treatment of illnesses which are connected with androgens.

In DE 22 26 552 B2, further 17-cyano-19-nor-androst-4-en-3-one compounds are described which show progestomimetic, antiandrogenic and antioestrogenic actions having exogenous character.

The object of the present invention is to make available compounds which have strong binding to the gestagen receptor. Moreover, the compounds should preferably also have an antimineralcorticoid action.

This object was achieved by the novel 17β-nor-cyano-19-androst-4-ene derivatives according to Formula I, the use of the novel derivatives for the production of a medicament for oral contraception and for the treatment of pre-, peri- and postmenopausal symptoms, and a medicament comprising at least one of the novel derivatives and a suitable pharmaceutically harmless additive. Advantageous embodiments of the invention are indicated in the subclaims.

The present invention accordingly relates to a 17β-cyano-19-nor-androst-4-ene derivative having the general chemical formula 1

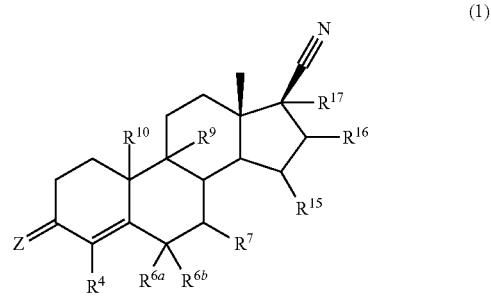

(1)

where
Z is selected from the group comprising 0, two hydrogen atoms, NOR and NNHSO$_2$R, in which R is hydrogen or C$_1$-C$_4$-alkyl,
R$^4$ is hydrogen or halogen,
furthermore either:
R$^{6a}$, R$^{6b}$ together form methylene or 1,2-ethanediyl or R$^{6a}$ is hydrogen and R$^{6b}$ is selected from the group comprising hydrogen, methyl and hydroxymethylene, and R$^7$ is selected from the group comprising hydrogen, C$_1$-C$_4$-alkyl, C$_2$-C$_3$-alkenyl and cyclopropyl,
or:
R$^{6a}$ is hydrogen and R$^{6b}$ and R$^7$ together form methylene or are omitted with formation of a double bond between C$^6$ and C$^7$
R$^9$, R$^{10}$ are hydrogen or are omitted with formation of a double bond between C$^9$ and C$^{10}$
R$^{15}$, R$^{16}$ are hydrogen or together form methylene,
R$^{17}$ is selected from the group comprising hydrogen, C$_1$-C$_4$-alkyl and allyl,
where at least one of the substituents R$^4$, R$^{6a}$, R$^{6b}$, R$^7$, R$^{15}$, R$^{16}$ and R$^{17}$ is unequal to hydrogen or R$^{6b}$ and R$^7$ are omitted with formation of a double bond between C$^6$ and C$^7$,
and its solvates, hydrates, stereoisomers, diastereomers, enantiomers and salts.

The numbering of the C ring system of the novel derivative of the general chemical formula 1 customarily follows the numbering of a steroid ring system, described, for example, in Fresenius, loc. cit. The numbering of the radicals indicated in the claims analogously corresponds to their bonding position to the C ring system of the derivative. For instance, the radical R$^4$ bonds to the C$^4$-position of the novel derivative.

With respect to the groups defined for Z, the groups NOR and NNHSO$_2$R in each case bond using a double bond via N to the C skeleton of the derivative as in =NOR and =N—NH—SO$_2$R. OR in NOR and NHSO$_2$R in NNHSO$_2$R can be in the syn or anti position.

C$_1$-C$_4$-Alkyl is in each case understood as meaning a straight-chain or branched alkyl radical, namely methyl, ethyl, n-propyl, isopropyl, n-butyl, isobutyl or tert-butyl. Particularly preferred are especially the unbranched radicals Methyl, ethyl and n-propyl. Methyl, ethyl and n-propyl are particularly preferred. Alkyl radicals bonded in the 17α position can moreover be perfluorinated, such that R$^{17}$ in this case can moreover be trifluoromethyl, pentafluoroethyl, n-heptafluoropropyl, isoheptafluoropropyl, n-nonafluorobutyl, isononafluorobutyl and tert-nonafluorobutyl.

$C_2$-$C_3$-Alkenyl is preferably to be understood as meaning vinyl or allyl.

Halogen is in each case to be understood as meaning fluorine, chlorine, bromine or iodine.

Isomers are chemical compounds having the same empirical formula, but different chemical structure. Expressly, all possible isomers and isomer mixtures (racemates) are additionally included, the 17β-cyano position being specified in the novel derivative.

In general, constitutional isomers and stereoisomers are differentiated. Constitutional isomers have the same empirical formula, but differ in the manner of linkage of their atoms or atomic groups. These include functional isomers, positional isomers, tautomers or valence isomers. In principle, stereoisomers have the same structure (constitution) and thus also the same empirical formula, but differ in the spatial arrangement of the atoms. In general, configurational isomers and conformational isomers are differentiated. Configurational isomers are stereoisomers which can only be converted into one another by bond breakage. These include enantiomers, diastereomers and E/Z (cis/trans) isomers. Enantiomers are stereoisomers which behave as image and mirror image to one another and have no plane of symmetry. All stereoisomers which are not enantiomers are designated as diastereomers. E/Z (cis/trans) isomers on double bonds are a special case. Conformational isomers are stereoisomers which can be converted into one another by the rotation of single bonds. For the delineation of the types of isomerism from one another see also the IUPAC rules, section E (Pure Appl. Chem. 45, 11-30 (1976)).

The novel derivatives having the general chemical formula 1 also comprise the possible tautomeric forms and include the E or Z isomers or, if a chiral centre is present, also the racemates and enantiomers. Double bond isomers are also to be understood among these.

The novel derivatives can also be present in the form of solvates, in particular of hydrates, the novel compounds accordingly containing polar solvents, in particular water, as a structural element of the crystal lattice of the novel compounds. The polar solvent, in particular water, can be present in a stoichiometric or alternatively unstoichiometric ratio. In the case of stoichiometric solvates, hydrates, hemi-, (semi-), mono-, sesqui-, di-, tri-, tetra-, penta-, etc. solvates or hydrates are also spoken of.

It has been found that the novel compounds or derivatives have a good gestagenic action in vivo. Moreover, some interesting novel compounds act as antagonists for the mineralcorticoid receptor.

Novel derivatives having the aforementioned general chemical formula 1 are preferred in which Z is selected from the group comprising O, NOH and NNHSO$_2$H. Z is particularly preferably O.

Independently of the selection of Z, novel derivatives having the aforementioned general chemical formula 1 are furthermore preferred in which the following variants occur alternatively or else at least in some cases together and are selected independently of one another:

$R^{15}$ and $R^{16}$ especially preferably together form methylene, where both an α- and a β-methylene group can be bonded in these positions.

$R^4$ is furthermore preferably hydrogen or chlorine.

$R^{6a}$ and $R^{6b}$ furthermore preferably together form 1,2-ethanediyl or are in each case hydrogen.

$R^7$ is furthermore preferably selected from the group comprising hydrogen and methyl, where the methyl group can be both α- and β-.

$R^{6b}$ and $R^7$ furthermore preferably together form methylene, where the methylene group can be both α- and β-.

$R^{17}$ is furthermore preferably selected from the group comprising hydrogen and methyl.

The radicals $R^{6a}$, $R^{6b}$, $R^7$, $R^{15}$ and $R^{16}$ can furthermore be both α- and β-.

The novel 17β-cyano-19-nor-androst-4-ene derivatives are particularly preferably selected from the group comprising:

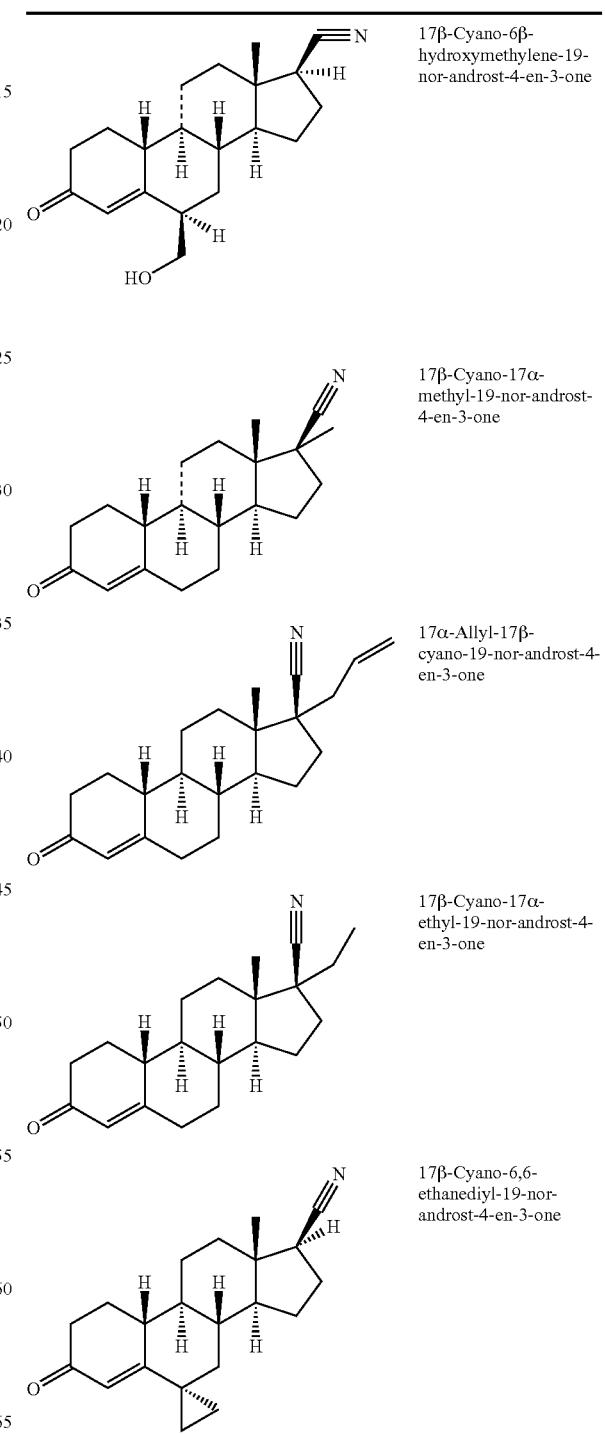

17β-Cyano-6β-hydroxymethylene-19-nor-androst-4-en-3-one

17β-Cyano-17α-methyl-19-nor-androst-4-en-3-one

17α-Allyl-17β-cyano-19-nor-androst-4-en-3-one

17β-Cyano-17α-ethyl-19-nor-androst-4-en-3-one

17β-Cyano-6,6-ethanediyl-19-nor-androst-4-en-3-one

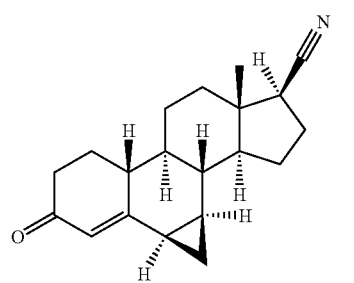 17β-Cyano-6β, 7β-methylene-19-nor-androst-4-en-3-one

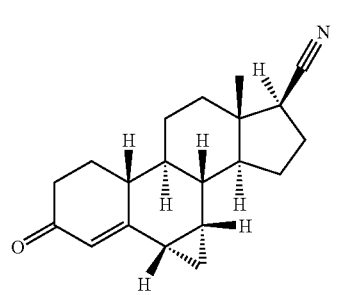 17β-Cyano-6α, 7α-methylene-19-nor-androst-4-en-3-one

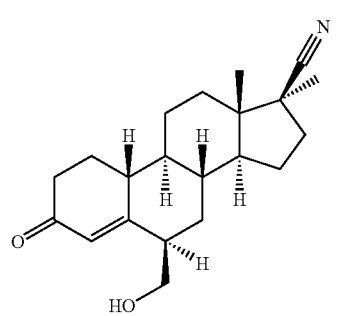 17β-Cyano-17α-methyl-6β-hydroxymethylene-19-nor-androst-4-en-3-one

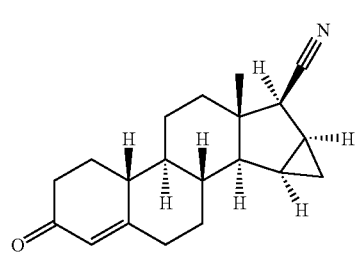 17β-Cyano-15β, 16β-methylene-19-nor-androst-4-en-3-one

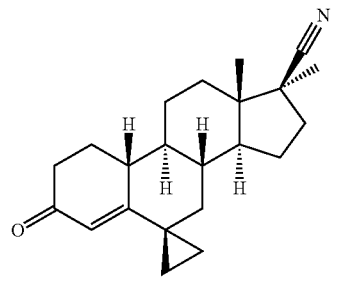 17β-Cyano-6,6-ethanediyl-17α-methyl-19-nor-androst-4-en-3-one

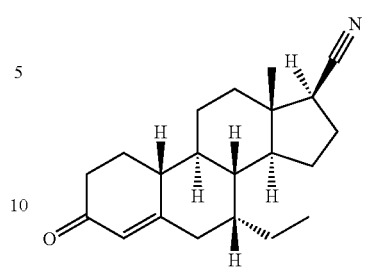 17β-Cyano-7α-ethyl-19-nor-androst-4-en-3-one

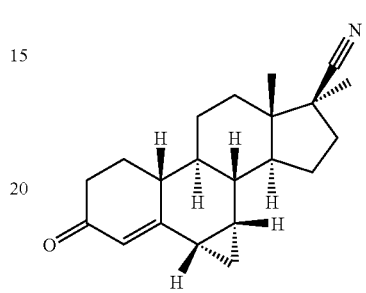 17β-Cyano-17α-methyl-6α,7α-methylene-19-nor-androst-4-en-3-one

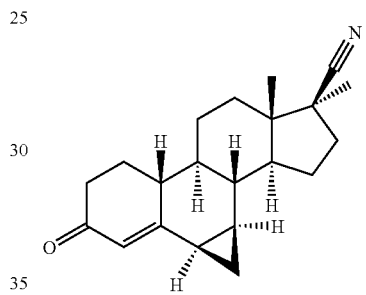 17β-Cyano-17α-methyl-6β,7β-methylene-19-nor-androst-4-en-3-one

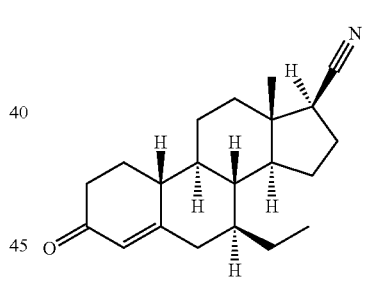 17β-Cyano-7β-ethyl-19-nor-androst-4-en-3-one

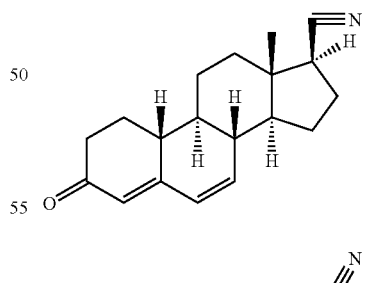 17β-Cyano-19-nor-androsta-4,6-dien-3-one

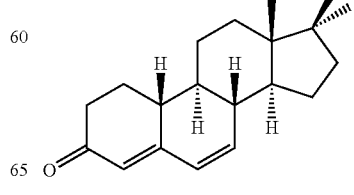 17β-Cyano-17α-methyl-19-nor-androsta-4,6-dien-3-one

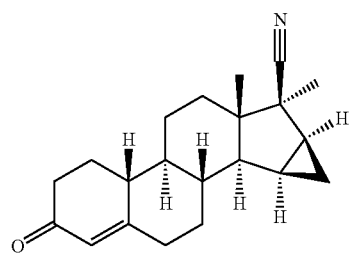 17β-Cyano-17α-methyl-15β,16β-methylene-19-nor-androst-4-en-3-one

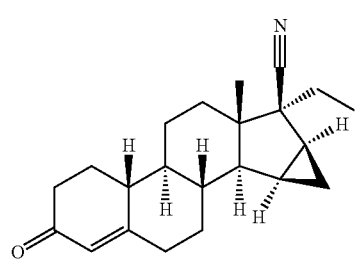 17β-Cyano-17α-ethyl-15β,16β-methylene-19-nor-androst-4-en-3-one

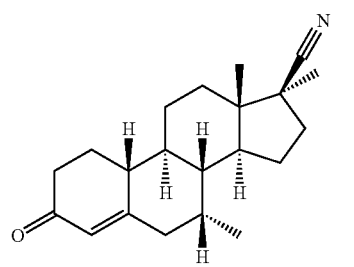 7α,17α-Bismethyl-17β-cyano-19-nor-androst-4-en-3-one

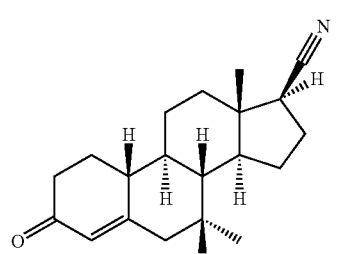 17β-Cyano-7α-methyl-19-nor-androst-4-en-3-one

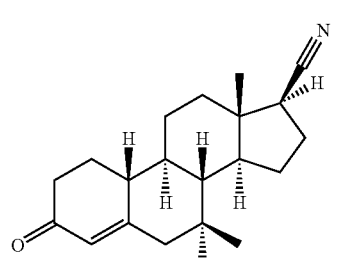 17β-Cyano-7β-methyl-19-nor-androst-4-en-3-one

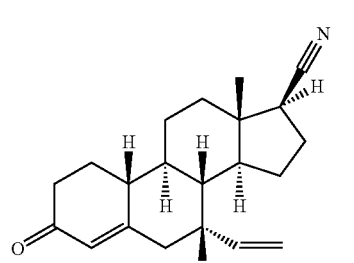 17β-Cyano-7α-vinyl-19-nor-androst-4-en-3-one

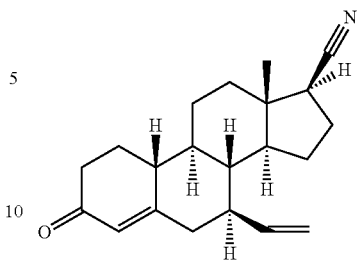 17β-Cyano-7β-vinyl-19-nor-androst-4-en-3-one

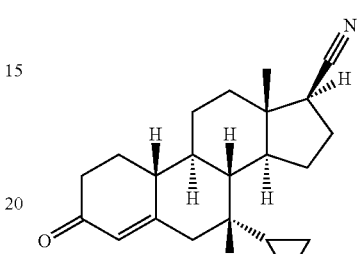 17β-Cyano-7α-cyclopropyl-19-nor-androst-4-en-3-one

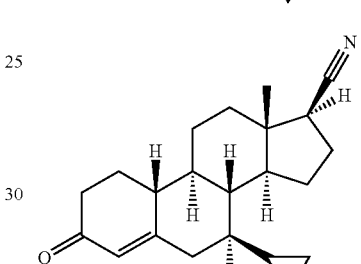 17β-Cyano-7β-cyclopropyl-19-nor-androst-4-en-3-one

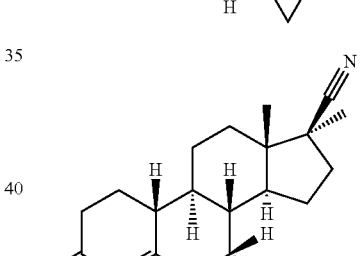 17β-Cyano-7α-cyclopropyl-17α-methyl-19-nor-androst-4-en-3-one

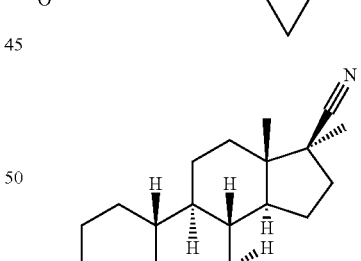 17β-Cyano-7β-cyclopropyl-17α-methyl-19-nor-androst-4-en-3-one

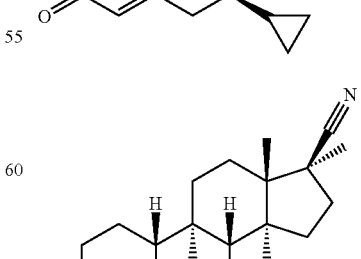 17β-Cyano-17α-methyl-7α-vinyl-19-nor-androst-4-en-3-one

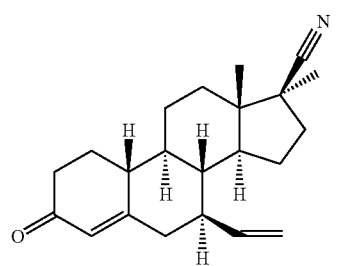

17β-Cyano-17α-methyl-7β-vinyl-19-nor-androst-4-en-3-one

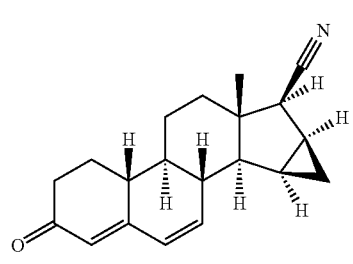

17β-Cyano-15βB,16β-methylene-19-nor-androsta-4,6-dien-3-one

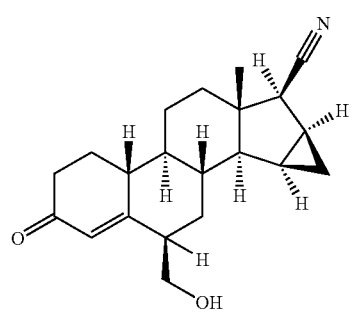

17β-Cyano-15β,16β-methylene-6β-hydroxymethyl-19-nor-androst-4-en-3-one

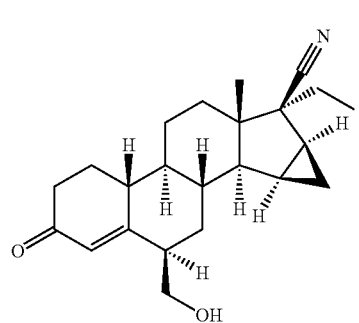

17α-Ethyl-17β-cyano-15β,16β-methylene-6β-hydroxymethyl-19-nor-androst-4-en-3-one

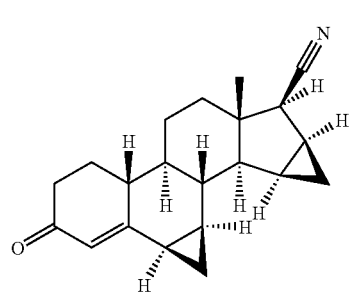

17β-Cyano-6β,7β-15β,16β-bismethylene-19-nor-androst-4-en-3-one

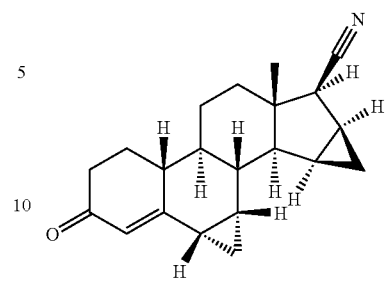

17β-Cyano-6α,7α-15β,16β-bismethylene-19-nor-androst-4-en-3-one

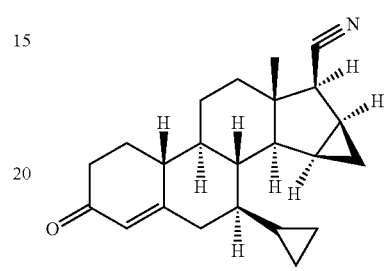

17β-Cyano-7β-cyclopropyl-15β,16β-methylene-19-nor-androst-4-en-3-one

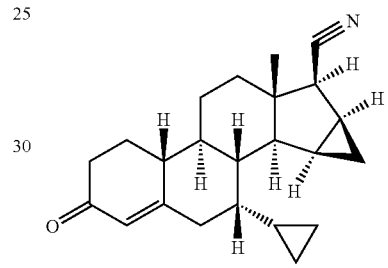

17β-Cyano-7α-cyclopropyl-15β,16β-methylene-19-nor-androst-4-en-3-one

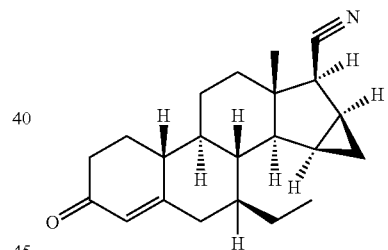

17β-Cyano-7β-ethyl-15β,16β-methylene-19-nor-androst-4-en-3-one

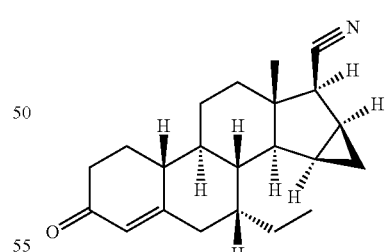

17β-Cyano-7α-ethyl-15β,16β-methylene-19-nor-androst-4-en-3-one

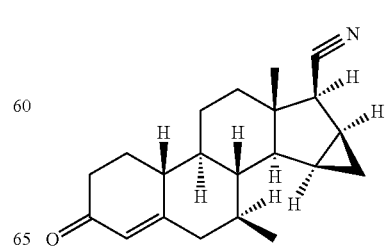

17β-Cyano-7β-methyl-15β,16β-methylene-19-nor-androst-4-en-3-one

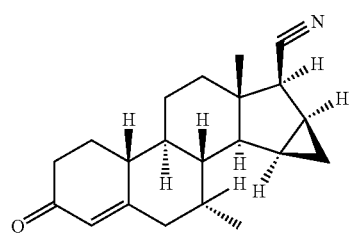 17β-Cyano-7α-methyl-15β,16β-methylene-19-nor-androst-4-en-3-one

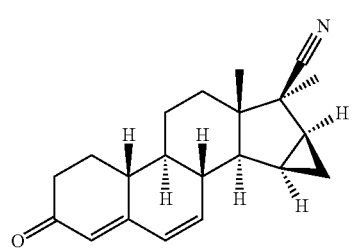 17β-Cyano-17α-methyl-15β,16β-methylene-19-nor-androsta-4,6-dien-3-one

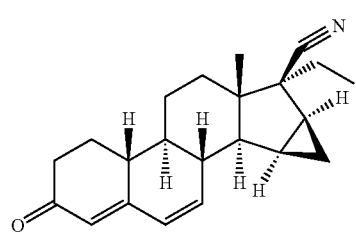 17β-Cyano-17α-ethyl-15β,16β-methylene-19-nor-androsta-4,6-dien-3-one

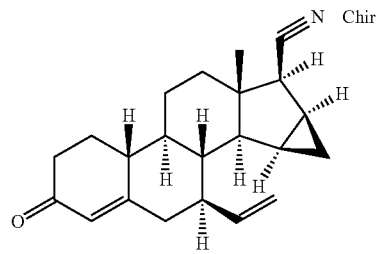 17β-Cyano-15β,16β-methylene-7β-vinyl-19-nor-androst-4-en-3-one

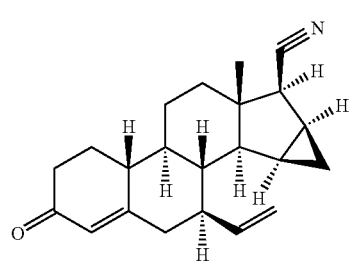 17β-Cyano-15β,16β-methylene-7α-vinyl-19-nor-androst-4-en-3-one

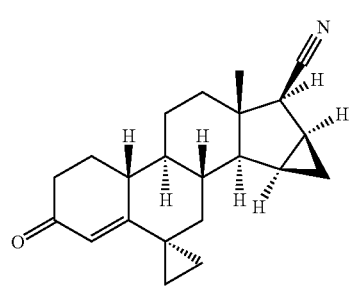 17β-Cyano-6,6-ethanediyl-15β,16β-methylene-19-nor-androst-4-en-3-one

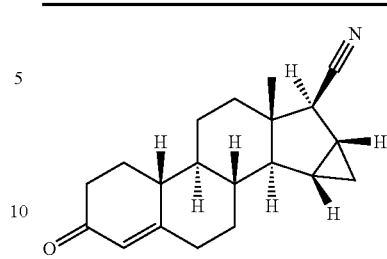 17β-Cyano-15α,16α-methylene-19-nor-androst-4-en-3-one

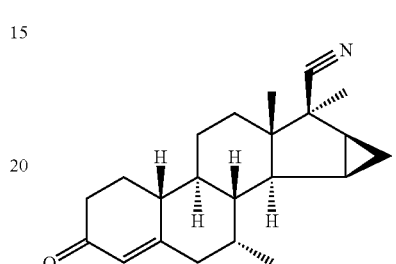 17β-Cyano-17α,7α-dimethyl-15β,16β-methylene-19-nor-androst-4-en-3-one

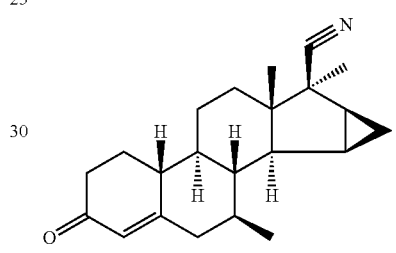 17β-Cyano-17α,7β-dimethyl-15β,16β-methylene-19-nor-androst-4-en-3-one

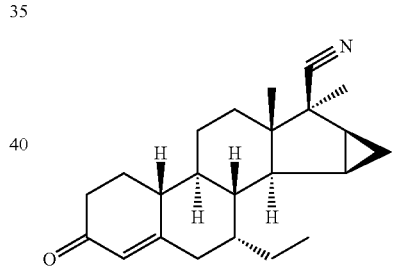 17β-Cyano-17α-methyl-7α-ethyl-15β,16β-methylene-19-nor-androst-4-en-3-one

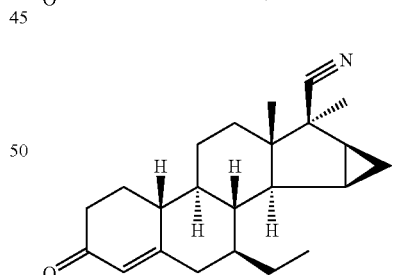 17β-Cyano-17α-methyl 7βB-ethyl-15β,16β-methylene-19-nor-androst-4-en-3-one

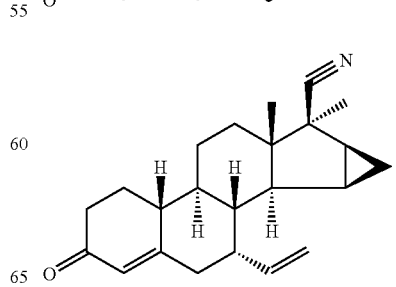 17β-Cyano-17α-methyl-7α-vinyl-15β,16β-methylene-19-nor-androst-4-en-3-one

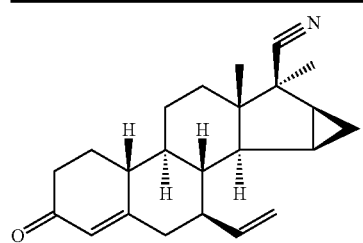
17β-Cyano-17α-methyl-7β-vinyl-15β,16β-methylene-19-nor-androst-4-en-3-one

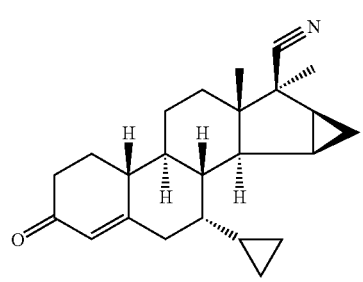
17β-Cyano-17α-methyl-7α-cyclopropyl-15β,16β-methylene-19-nor-androst-4-en-3-one

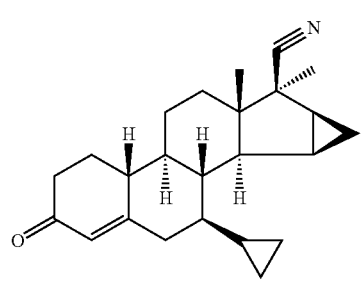
17β-Cyano-17α-methyl-7β-cyclopropyl-15β,16β-methylene-19-nor-androst-4-en-3-one

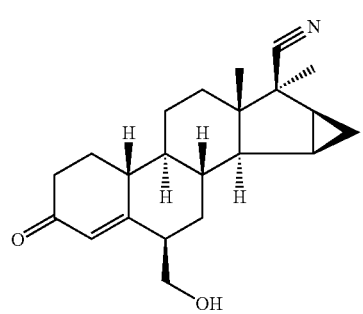
17β-Cyano-17α-methyl-6β-hydroxymethyl-15β,16β-methylene-19-nor-androst-4-en-3-one

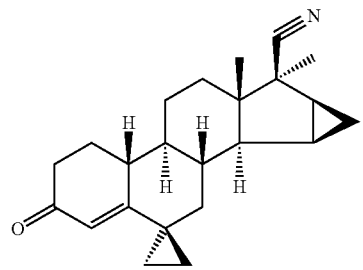
17β-Cyano-17α-methyl-6,6-ethylene-15β,16β-methylene-19-nor-androst-4-en-3-one

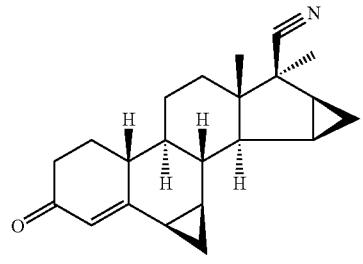
17β-Cyano-17α-methyl-6β,7β-methylene-15β,16β-methylene-19-nor-androst-4-en-3-one

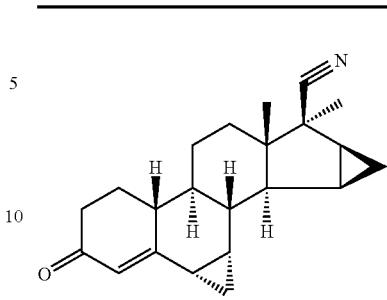
17β-Cyano-17α-methyl-6α,7α-methylene-15β,16β-methylene-19-nor-androst-4-en-3-one

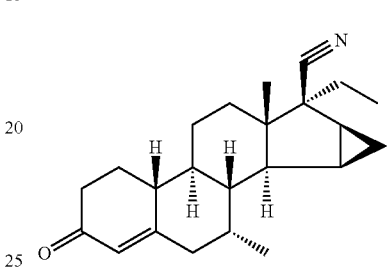
17β-Cyano-17α-ethyl-7α-methyl-15β,16β-methylene-19-nor-androst-4-en-3-one

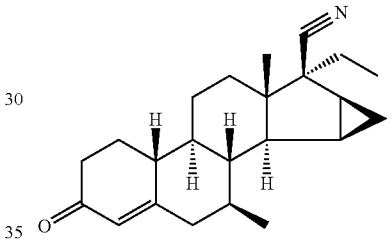
17β-Cyano-17α-ethyl-7β-methyl-15β,16β-methylene-19-nor-androst-4-en-3-one

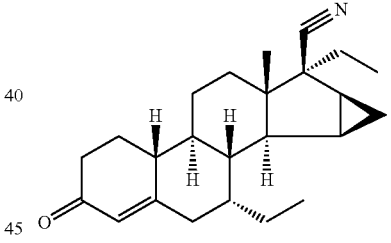
17β-Cyano-17α,7α-diethyl-15β,16β-methylene-19-nor-androst-4-en-3-one

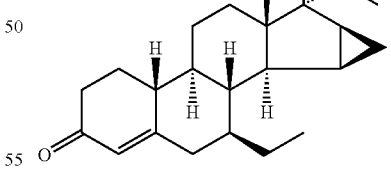
17β-Cyano-17α,7β-diethyl-15β,16β-methylene-19-nor-androst-4-en-3-one

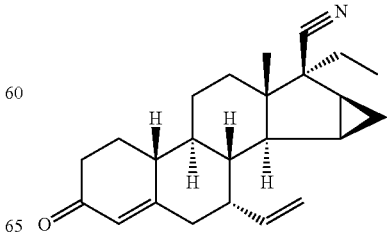
17β-Cyano-17α-ethyl-7α-vinyl-15β,16β-methylene-19-nor-androst-4-en-3-one

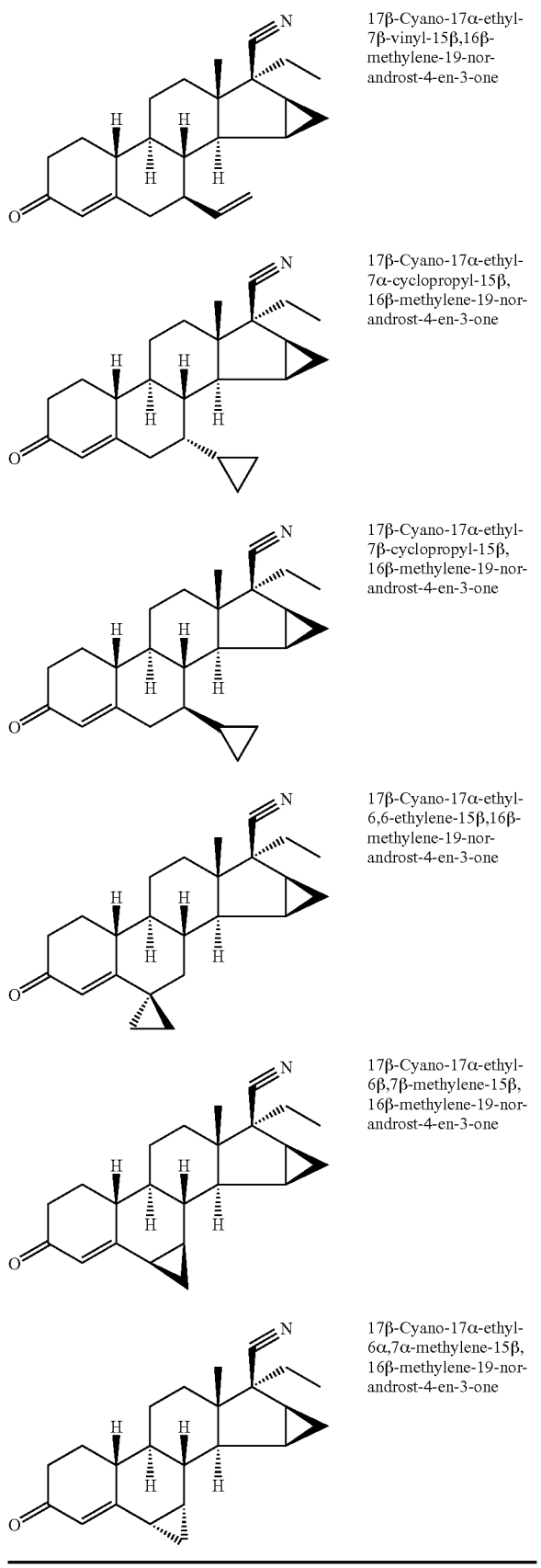

17β-Cyano-17α-ethyl-7β-vinyl-15β,16β-methylene-19-nor-androst-4-en-3-one

17β-Cyano-17α-ethyl-7α-cyclopropyl-15β,16β-methylene-19-nor-androst-4-en-3-one

17β-Cyano-17α-ethyl-7β-cyclopropyl-15β,16β-methylene-19-nor-androst-4-en-3-one

17β-Cyano-17α-ethyl-6,6-ethylene-15β,16β-methylene-19-nor-androst-4-en-3-one

17β-Cyano-17α-ethyl-6β,7β-methylene-15β,16β-methylene-19-nor-androst-4-en-3-one

17β-Cyano-17α-ethyl-6α,7α-methylene-15β,16β-methylene-19-nor-androst-4-en-3-one

The 15α,16α- and the 15β,16β-methylene derivatives in the above list are very particularly preferred.

On account of their gestagenic activity, the novel compounds having the general chemical formula 1 can be used alone or in combination with oestrogens in medicaments for contraception.

The derivatives according to the invention are therefore suitable in particular for the production of a medicament for oral contraception and for the treatment of pre-, peri- and postmenopausal symptoms, including use in preparations for hormone replacement therapy (HRT).

Because of their favourable profile of action, the derivatives according to the invention are particularly highly suitable for the treatment of premenstrual symptoms, such as headaches, depressive disgruntlements, water retention and mastodynia.

The use of the derivatives according to the invention for the production of a medicament having gestagenic and antimineralcorticoid action is particularly preferred.

Treatment with the derivatives according to the invention preferably takes place in humans, but can also be carried out on related mammalian species, such as, for example, on dog and cats.

For the use of the derivatives according to the invention as medicaments, these are combined with at least one suitable pharmaceutically harmless additive, for example vehicle. The additive is suitable, for example, for parenteral, preferably oral, administration. It is a matter here of pharmaceutically suitable organic or inorganic inert additive materials, such as, for example, water, gelatine, gum arabicum, lactose, starch, magnesium stearate, talc, vegetable oils, polyalkylene glycols etc. The medicaments can be present in solid form, for example as tablets, coated tablets, suppositories, capsules, or in liquid form, for example as solutions, suspensions or emulsions. Optionally, they moreover contain excipients, such as preservatives, stabilizers, wetting agents or emulsifiers, salts for changing the osmotic pressure or buffers. For parenteral administration, oily solutions, such as, for example, solutions in sesame oil, castor oil and cottonseed oil, are in particular suitable. To increase the solubility, solubilizers, such as, for example, benzyl benzoate or benzyl alcohol, can be added. It is also possible to incorporate the derivatives according to the invention into a transdermal system and thus to administer it transdermally. For oral administration, tablets, coated tablets, capsules, pills, suspensions or solutions are in particular suitable.

The dose of the derivatives according to the invention in contraception preparations should be 0.01 to 10 mg per day. The daily dose in the case of the treatment of premenstrual symptoms is approximately 0.1 to 20 mg. The gestagenic derivatives according to the invention are preferably administered orally in contraception preparations and in the medicaments for the treatment of premenstrual symptoms. The daily dose is preferably administered as a single dose.

The gestagenic and oestrogenic active substance components are preferably administered together orally in contraception preparations. The daily dose is preferably administered as a single dose.

Possible oestrogens are synthetic oestrogens, preferably ethinylestradiol, but also mestranol.

The oestrogen is administered in a daily amount which corresponds to that of 0.01 to 0.04 mg of ethinylestradiol.

Oestrogens, of course, are primarily used as oestrogens in the medicaments for the treatment of pre-, peri- and postmenopausal symptoms and for hormone replacement therapy, especially oestradiol or its esters, for example oestradiol valerate, or alternatively conjugated oestrogens (CEEs=Conjugated Equine Estrogens).

If the preparation of the starting compounds is not described here, these are known to the person skilled in the art or can be prepared analogously to known compounds or processes described here. The isomer mixtures can be separated into the enantiomers, E/Z isomers or epimers by customary methods, such as, for example, crystallization, chromatography or salt formation.

The derivatives according to the invention having the general chemical formula 1 are prepared as described below.

Suitable starting materials for the 17β-cyano-19-nor-androst-4-en-3-one derivatives described here are various steroidal starting materials, such as, for example, 19-nor-androst-4-ene-3,17-dione, or alternatively the partially reduced analogues.

Microbiologically, for example, 15α-hydroxy-19-nor-androst-4-ene-3,17-dione is accessible, which opens up access to 15β,16β-methylenated 17-cyanosteroids, for this see examples in the experimental section. 15α,16α6-Methylenated precursors which are suitable for the synthesis of the corresponding 17-cyanosteroids are likewise known, e.g. 17β-hydroxy-15α,16α-methylene-19-nor-androst-4-en-3-one in DE-A 22 07 421 (1973). Access to 17β-cyano-19-nor-androst-4-en-3-one is described in DE-A 22 26 552.

It is obvious to the person skilled in the art that in the descriptions of the synthetic transformations it is always provided for other functional groups optionally present on the steroid ring system to be protected in suitable form.

The introduction of a nitrile into position 17 ($C^{17}$) of the steroid ring system can be carried out in a variety of ways. Both single-stage processes and multistage variants are possible here. Methods are preferred here which finally mean the replacement of an oxygen function by cyanide. Many possible process variants are described in *Science of Synthesis* Houben-Weyl Methods of Molecular Transformations Category 3 Volume 19 pp. 197-213 (2004 Georg Thieme Verlag Stuttgart, New York) and in *Houben-Weyl Methoden der organischen Chemie [Houben-Weyl Methods of organic chemistry]* Volume E5 Part 2 pp. 1318-1527 (1985 Georg Thieme Verlag Stuttgart, New York).

A single-stage process which suggests itself is, for example, the direct reductive replacement of a carbonyl oxygen atom by a cyano group. For this, a 17-ketosteroid is reacted with tosylmethyl isocyanide in suitable solvents, such as, for example, dimethoxyethane, dimethyl sulphoxide, ethers, alcohols or alternatively their mixtures, using suitable bases, such as, for example, alkali metal alkoxides, alkali metal hydrides, potassium hexamethyldisilazide, or alternatively alkali metal amides, such as, for example, lithium diisopropylamide, in a temperature range from 0° C. to 100° C. 17-Epimer mixtures which may be formed can be separated by chromatography, fractional crystallization or using a combination of these methods.

The $SN_2$-type replacement of a suitable leaving group in position 17, such as, for example, of a halide (preferably iodine or bromine), or alternatively of a sulphonic acid ester of a 17-alcohol, by cyanide is also possible. Cyanide sources used are preferably inorganic cyanides, such as lithium cyanide, sodium cyanide and potassium cyanide.

The following may be mentioned as examples of multi-stage variants of nitrile introduction: a 17-ketone is converted by means of a Wittig olefination to the corresponding 17-exomethylene compound, which after hydroboration and oxidation to the aldehyde can be reacted to give the corresponding 17-carbaldehyde oxime. Dehydration of the oxime then leads to the 17-nitrile.

The introduction of the nitrile can be carried out both at the beginning of a synthesis sequence and also at any desired later point in time, provided that further functional groups which may be present are protected in a suitable manner.

The 17-cyano compounds can be optionally alkylated, which leads to stereochemically homogeneous 17β-cyano-17α-substituted derivatives. For this, the 17-cyanosteroid is deprotonated in a suitable solvent, such as, for example, ethers, for example tetrahydrofuran. Various bases can be used here, for example an alkali metal amide, such as lithium diisopropylamide. After addition of an alkylating agent, such as, for example, of an alkyl or alkenyl halide, and work-up, the 17β-cyano-17α-substituted derivatives are then obtained.

By way of example, the further synthetic procedure may be illustrated with the aid of the following synthesis scheme, the compound 2 (DE-A 22 26 552 (1972)) already described being mentioned as a starting material:

Scheme 1

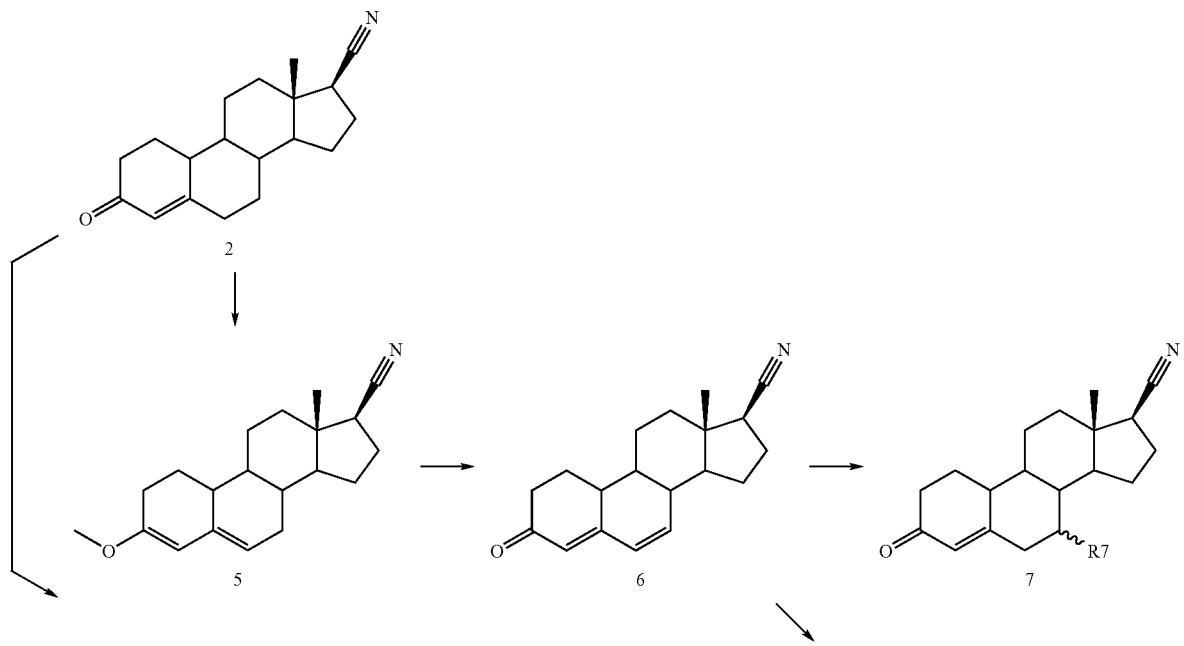

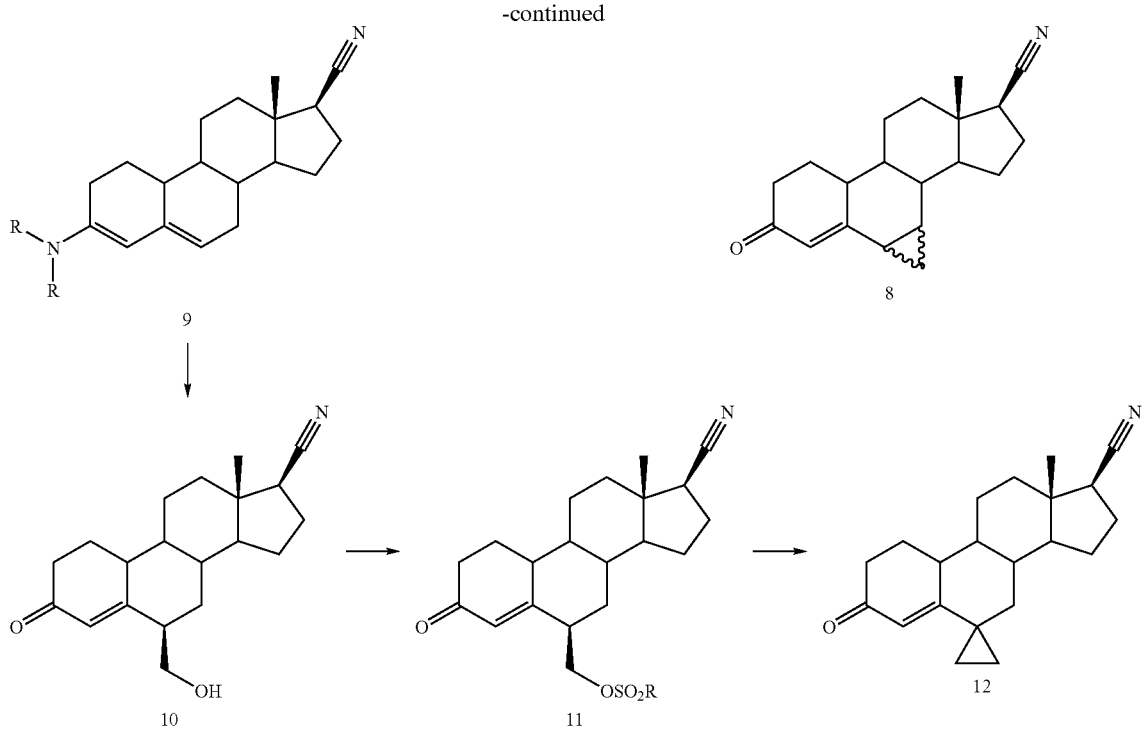

The introduction of a 6,7-double bond is carried out by means of bromination of the 3,5-dienol ether 5 and subsequent elimination of hydrogen bromide (see, for example, J. Fried, J. A. Edwards, *Organic Reactions in Steroid Chemistry*, von Nostrand Reinhold Company 1972, pp. 265-374).

The introduction of a substituent $R^4$ can be achieved, for example, starting from a compound of the formula 2, by epoxidation of the 4,5-double bond with hydrogen peroxide under alkaline conditions and reaction of the resulting epoxides in a suitable solvent with acids having the general chemical formula H—$R^4$, where $R^4$ can be a halogen atom or a pseudohalogen, or by reacting with catalytic amounts of mineral acid and optionally reacting the 4-bromo compounds obtained having the general chemical formula 1 (where $R^4$=bromine) with methyl 2,2-difluoro-2-(fluorosulphonyl)-acetate in dimethylformamide in the presence of copper(I) iodide.

The dienol ether bromination of compound 5 can be carried out, for example, analogously to the procedure of *Steroids* 1, 233 (1963). The elimination of hydrogen bromide is possible by heating the 6-bromo compound with basic reagents, such as, for example, LiBr or $Li_2CO_3$, in aprotic solvents, such as dimethylformamide, at temperatures from 50° C. to 120° C. or else by heating the 6-bromo compounds in a solvent, such as collidine or lutidine, to give compound 6.

Compound 7 is converted by methenylation of the 6,7-double bond according to known processes, for example using dimethylsulphoxonium methylide (see, for example, DE-A 11 83 500, DE-A 29 22 500, EP-A 0 019 690, U.S. Pat. No. 4,291,029; *J. Am. Chem. Soc.* 84, 867 (1962)) to a compound 8, a mixture of the α- and β-isomers being obtained, which can be separated into the individual isomers, for example, by chromatography.

Compounds of the type 7 can be obtained as described in the examples or analogously to these procedures using reagents analogous to those described there.

The synthesis of the spirocyclic compound 12 starts from 2, which is first converted to a 3-amino-3,5-diene derivative 9. By reaction with formalin in alcoholic solution, the 6-hydroxymethylene derivative 10 is obtained. After conversion of the hydroxyl group to a leaving group, such as, for example, a mesylate, tosylate (compound 11) or alternatively benzoate, compound 13 can be prepared by reaction with trimethylsulphoxonium iodide using bases, such as, for example, alkali metal hydroxides or alkali metal alkoxides, in suitable solvents, such as, for example, dimethyl sulphoxide.

For the introduction of a 6-methylene group, compound 10 can be dehydrated using, for example, hydrochloric acid in dioxane/water. 6-Methylene can also be produced from 11 (see DE-A 34 02 3291, EP-A 0 150 157, U.S. Pat. No. 4,584, 288; *J. Med. Chem.* 34, 2464 (1991)).

A further possibility for the preparation of 6-methylene compounds consists in the direct reaction of the 4(5) unsaturated 3-ketones, such as compound 2, with acetals of formaldehyde in the presence of sodium acetate using, for example, phosphorus oxychloride or phosphorus pentachloride in suitable solvents, such as chloroform (see, for example, K. Annen, H. Hofineister, H. Laurent and R. Wiechert, *Synthesis* 34 (1982)).

The 6-methylene compounds can be used for the preparation of compounds having the general formula 1, in which $R^{6a}$ is equal to methyl and $R^{6b}$ and $R^7$ are omitted with formation of a double bond between $C^6$ and $C^7$.

For this, for example, a process described in *Tetrahedron* 21, 1619 (1965) can be used, in which an isomerization of the double bond is achieved by warming the 6-methylene compounds in ethanol with 5% palladium-carbon catalyst, which was pretreated either with hydrogen or by warming with a small amount of cyclohexene. The isomerization can also be carried out using a catalyst which was not pretreated, if a small amount of cyclohexene was added to the reaction mixture. The occurrence of small amounts of hydrogenated products can be prevented by addition of an excess of sodium acetate.

The 6-methyl-4,6-dien-3-one derivatives, however, can also be prepared directly (see K. Annen, H. Hofineister, H. Laurent and R. Wiechert, *Lieb. Ann.* 712 (1983)).

Compounds in which $R^{6b}$ is an α-methyl function can be prepared from the 6-methylene compounds by hydrogenation under suitable conditions. The best results (selective hydrogenation of the exo-methylene function) are achieved by transfer hydrogenation (*J. Chem. Soc.* 3578 (1954)). If the 6-methylene derivatives are heated in a suitable solvent, such as, for example, ethanol, in the presence of a hydride donor, such as, for example, cyclohexene, 6α-methyl derivatives are obtained in very good yields. Small amounts of 6β-methyl compound can be isomerized by acid (*Tetrahedron* 1619 (1965)).

The selective preparation of 6β-methyl compounds is also possible. For this, the 4-en-3-ones, such as, for example, compound 2, are reacted, for example, with ethylene glycol or trimethyl orthoformate in dichloromethane in the presence of catalytic amounts of an acid, e.g. p-toluenesulphonic acid, to give the corresponding 3-ketals. During this ketalization, the double bond in position 5 ($C^5$) isomerizes. A selective epoxidation of this 5-double bond is possible, for example, by use of organic peracids, e.g. of m-chloroperbenzoic acid, in suitable solvents, such as dichloromethane. Alternatively to this, the epoxidation can also be carried out using hydrogen peroxide in the presence of, for example, hexachloroacetone or 3-nitrotrifluoroacetophenone. The 5,6α-epoxides can then be opened axially using appropriate alkylmagnesium halides or alkyllithium compounds. 5α-Hydroxy-6β-alkyl compounds are thus obtained. The cleavage of the 3-keto protective group can be carried out with obtainment of the 5α-hydroxyl function by treating under mild acidic conditions (acetic acid or 4 N hydrochloric acid at 0° C.). Basic elimination of the 5α-hydroxyl function using, for example, diluted aqueous sodium hydroxide solution affords the 3-keto-4-ene compounds having a β-6-alkyl group. Alternatively to this, ketal cleavage under more drastic conditions (aqueous hydrochloric acid or another strong acid) affords the corresponding 6α-alkyl compounds.

The compounds having the general chemical formula 1 obtained, in which Z is an oxygen atom, can be converted to their corresponding oximes (general chemical formula 1 with Z denoting NOH, where the hydroxyl group can be syn- or anti-) by reaction with hydroxylamine hydrochloride in the presence of a tertiary amine at temperatures between −20 and +40° C. Suitable tertiary bases are, for example, trimethylamine, triethylamine, pyridine, N,N-dimethylaminopyridine, 1,5-diazabicyclo[4.3.0]non-5-ene (DBN) and 1,5-diazabicyclo[5.4.0]undec-5-ene (DBU), pyridine being preferred. This applies analogously as is described in WO-A 98/24801 for the preparation of corresponding 3-oxyimino derivatives of drospirenone.

The removal of the 3-oxo group for the preparation of a final product having the general chemical formula 1 with Z denoting two hydrogen atoms can be carried out, for example, by reductive cleavage of a thioketal of the 3-keto compound according to the procedure indicated in DE-A 28 05 490.

The following examples serve for the more detailed illustration of the invention:

The compounds according to the invention are surprisingly distinguished by strong gestagenic activity and are strongly active in the maintenance of pregnancy test on the rat after subcutaneous administration.

Carrying out the maintenance of pregnancy test on the rat:

In pregnant rats, the removal of the corpora lutea or oophorectomy induces an abortion. By means of the exogenous administration of progestins (gestagens) in combination with a suitable dose of an oestrogen, the maintenance of pregnancy is possible. The maintenance of pregnancy test on ovarectomized rats serves for the determination of the peripheral gestagenic activity of a compound.

Rats were paired overnight during proestrus. Pairing was checked on the morning of the following day by the appraisal of a vaginal smear. The presence of the sperm was evaluated here as day 1 of a commencing pregnancy. On day 8 of the pregnancy, the animals were ovarectomized under ether anaesthesia. The treatment with test compound and exogenous oestrogen (oestrone, 5 μg/kg/day) was carried out subcutaneously once daily from day 8 to day 15 or day 21 of the pregnancy. The first administration on day 8 was carried out two hours before oophorectomy. Intact control animals were given exclusively vehicle.

Evaluation:

At the end of the experiment (day 15 or day 21), the animals were sacrificed under a $CO_2$ atmosphere, and live foetuses (foetuses having a beating heart) and implantation sites (early resorptions and dead foetuses including autolysis and atrophic placentas) were counted in both uterine horns. On day 22, it was moreover possible to examine foetuses for malformations. In uteri without foetuses or implantation sites, the number of nidation sites was determined by staining with 10% strength ammonium sulphide solution. The maintenance of pregnancy rate was calculated as the quotient of the number of living foetuses and the total number of nidation sites (both resorbed and dead foetuses and nidation sites). For certain test substances, the pregnancy-maintaining doses (ED50) indicated in Table 1 were determined. For drospirenone, this value is 3.5 mg/kg/day.

The derivatives according to the invention having the general chemical formula 1 have a very strong gestagenic activity. It was moreover found that the derivatives according to the invention show antimineralcorticoid action in vitro. They should therefore have in vivo potassium-retaining, natriuretic (antimeralcorticoid) action. These properties were determined using the test described below:

For the culturing of the cells used for the assay, the culture medium used was DMEM (Dulbecco's Modified Eagle Medium: 4500 mg/ml of glucose; PAA, #E15-009) with 10% FCS (Biochrom, S0115, batch #615B), 4 mM L-glutamine, 1% penicillin/streptomycin, 1 mg/ml of G418 and 0.5 μg/ml of puromycin.

Reporter cell lines were grown in a density of $4 \times 10^4$ cells per hollow in white, nontransparent tissue culture plates in each case having 96 hollows (PerkinElmer, #P12-106-017) and kept in 6% DCC—FCS (activated carbon-treated serum, for the removal of interfering components contained in the serum). The compounds to be investigated were added eight days later, and the cells were incubated with the compounds for 16 hours. The experiments were carried out in triplicate. At the end of the incubation, the effector-containing medium was removed and replaced by lysis buffer. After luciferase assay substrate (promega, #E1501) had been added, the plates containing the 96 hollows were then introduced into a microplate luminometer (Pherastar, BMG labtech), and the luminescence was measured. The IC50 values were evaluated using software for the calculation of dose-activity relationships. Experimental results are presented in Table 1:

TABLE 1

| Compound | MR Antagonism IC50 [nM] | MR Antagonism activity [% of the maximum effect] | PR in vivo ED50 [mg/kg/d s.c.] |
|---|---|---|---|
| 17β-Cyano-15α,16α-methylene-19-nor-androst-4-en-3-one | 16.0 | 93.01 | 0.8 |
| 17β-Cyano-17α-methyl-15β,16β-methylene-19-nor-androst-4-en-3-one | 29.0 | 96.00 | 0.8 |
| 7α,17α-Bismethyl-17β-cyano-19-nor-androst-4-en-3-one | 31.0 | 96.20 | 1.0 |
| 17β-Cyano-15β,16β-methylene-19-nor-androst-4-en-3-one | 4.5 | 95.57 | 0.84 |
| 17β-Cyano-17α-ethyl-15β,16β-methylene-19-nor-androst-4-en-3-one | 440 | 106.4 | 1.9 |
| 17β-Cyano-7α-methyl-19-nor-androst-4-en-3-one | 8.2 | 108.02 | 0.33 |
| 17β-Cyano-15β,16β-methylene-19-nor-androsta-4,6-dien-3-one | 15 | 108.51 | 3.3 |
| 17β-Cyano-17α-methyl-15β,16β-methylene-19-nor-androsta-4,6-dien-3-one | 190 | 114 | 2.1 |
| 17β-Cyano-7α-methyl-15β,16β-methylene-19-nor-androst-4-en-3-one | 8.3 | 108.4 | 0.11 |
| 17β-Cyano-7α-methyl-15β,16β-methylene-19-nor-androst-4-en-3-one | 10.3 | 110 | 2.9 |
| 17β-Cyano-17α-ethyl-6α,7α-methylene-15β,16β-methylen-19-nor-androst-4-en-3-one | 90.17 | 160 | 0.22 |

The following examples for the synthesis of preferred compounds serve for the further illustration of the invention. The new intermediates disclosed in the individual synthesis examples are, just like the 17β-cyano-19-nor-androst-4-ene derivatives according to the invention, essential to the invention.

Many of the reactions described below lead to epimer mixtures. Usually, the chromatographic separation of these mixtures via preparative HPLC is carried out under the following conditions: separations were carried out on a chiral normal phase, the stationary phase usually used being Chiralpak AD-H 5μ. Customarily, elution was carried out using a mixture of hexane and ethanol. In some cases, however, other eluent mixtures, such as, for example, mixtures of methanol and ethanol, were used:

EXAMPLE 1

17β-Cyano-15β,16β-methylene-19-nor-androst-4-en-3-one

1a

15α-Acetoxy-19-nor-androst-4-ene-3,17-dione 95 g of 15α-hydroxy-19-nor-androstenedione (described in DE-A 24 56 068; 1976) were dissolved in 332 ml of pyridine. After addition of 166 ml of acetic anhydride, the solution was stirred at room temperature for three hours. The reaction mixture was then poured into a mixture consisting of 10 l of ice water, 109 ml of conc. sulphuric acid and 16 ml of methanol. After stirring overnight, the precipitate was filtered off with suction and the filter residue was washed with 3 litres of water. 15α-Acetoxy-19-nor-androst-4-ene-3,17-dione was obtained, which was reacted further without purification.

1b

15α-Acetoxy-3-methoxy-19-nor-androsta-3,5-dien-17-one 90.6 g of the compound described in Example 1a were suspended in 955 ml of 2,2-dimethoxypropane and treated with 10.3 g of pyridinium tosylate. After heating the reaction mixture to 100° C. for 6.5 hours, it was stirred overnight at RT. After addition of 13.8 ml of pyridine, it was partially concentrated under reduced pressure on a rotary evaporator and the remaining flask contents were treated with 550 ml of methanol. After stirring at room temperature for one and a half hours, the mixture was cooled to 0° C., filtered off with suction and the filter cake was dried. 15α-Acetoxy-3-methoxy-19-nor-androsta-3,5-dien-17-one was thus obtained.

$^1$H-NMR (d6-DMSO): 0.87 (s, 3H, 18-CH3), 1.98 (s, 3H, CH3—CO—), 3.46 (s, 3H, 3-O—CH3), 5.10 (m, 1H, H-15), 5.18 (s, 1H, H-4), 5.21 (m, 1H, H-6)

1c

15β,16β-Methylene-3-methoxy-19-nor-androsta-3,5-dien-17-one 26.03 g of trimethylsulphoxonium iodide and 8.3 g of powdered sodium hydroxide were stirred in 344 ml dimethyl sulphoxide at a bath temperature of 50° C. for 30 minutes. The solution thus obtained was added dropwise in the course of 5 minutes to a suspension of 33.4 g of the compound described in Example 1b in 110 ml of dimethyl sulphoxide. After 20 minutes, the batch was transferred to a beaker and 500 ml of water were slowly added dropwise with stirring. After the mixture had been stirred for 20 minutes, it was filtered off with suction through a frit and the filter cake was dried. 15β,16β-Methylene-3-methoxy-19-nor-androsta-3,5-dien-17-one was obtained.

$^1$H-NMR (d6-DMSO): 0.91 (s, 3H, 18-CH3), 3.51 (s, 3H, 3-O—CH3), 5.26 (s, 1H, H-4), 5.33 (m, 1H, H-6)

1d

17-Cyano-15β,16β-methylene-3-methoxy-19-nor-androsta-3,5-diene 2.5 g of the compound described in Example 1c were initially introduced into a mixture of 40 ml of 1,2-dimethoxyethane and 25 ml of tertiary-butanol. After introduction of 4.7 g of potassium tertiary butoxide, 2.77 g of tosylmethyl isocyanide (TOSMIC) were added, and the mixture was stirred for 90 minutes. The batch was added to the tenfold amount of ice water, common salt was added to saturation and the mixture was filtered. The filter cake was taken up in ethyl acetate, the solution was washed with water and common salt solution, dried over sodium sulphate and filtered and the filtrate was concentrated. A mixture of 17α-cyano- and 17β-cyano-15β,16β-methylene-3-methoxy-19-nor-androsta-3,5-diene was obtained, which was reacted further without purification.

1e

17β-Cyano-15β,16β-methylene-19-nor-androst-4-en-3-one 2.8 g of the crude isomer mixture described in Example 1d were stirred for 3 hours in a mixture of 100 ml of acetone and 10 ml of 1 normal HCl. After neutralization of the reaction mixture with saturated sodium hydrogencarbonate solution, it was extracted with ethyl acetate and the organic phase was subsequently washed with water and saturated common salt solution. After drying over sodium sulphate, it was filtered, the filtrate was concentrated and the residue was first chromatographed on silica gel with a gradient of the solvents n-hexane and ethyl acetate. The product-containing fractions were then chromatographed again on silica gel using a mixture of n-hexane and ethyl acetate.

The fractions mainly containing the desired product were combined, concentrated and recrystallized from a mixture of diisopropyl ether and acetone. 17β-Cyano-15β,16β-methylene-19-nor-androst-4-en-3-one was obtained as a crystallizate. The mother liquor and the residual product-containing fractions from the chromatography afforded, after concentration, a mixture of 17α-cyano- and 17β-cyano-15β,16β-methylene-19-nor-androst-4-en-3-one.

$^1$H-NMR (300 MHz, CDCl$_3$ TMS as internal standard, selected signals): δ=0.46 (m, 1H), 0.90 (m, 1H), 1.04 (m, 1H), 1.10 (s, 3H, 18-CH3), 1.67 (m, 1H), 1.86 (m, 2H), 2.11 (m, 2H), 2.55 (m, 1H), 2.77 (d broad, 1H, J=4.4 Hz, 17-H), 5.86 (s, 1H, H-4)

EXAMPLE 2

17β-Cyano-15β,16β-methylene-19-nor-androsta-4,6-dien-3-one

2a

17β-Cyano-15β,16β-methylene 3-methoxy-19-nor-androsta-3,5-diene 9 g of 17β-cyano-15β,16β-methylene-19-nor-androst-4-en-3-one (see Example 1e), dissolved in 92 ml of methanol, were treated with 83 ml of methyl orthoformate. After addition of 53 mg of p-toluenesulphonic acid, the mixture was stirred at 15° C. A precipitate was formed. After addition of 0.8 ml of pyridine at 0° C., the mixture was cooled to −10° C. and stirred for 30 minutes. After concentration under reduced pressure, 17β-cyano-15β,16β-methylene 3-methoxy-19-nor-androsta-3,5-diene was obtained, which was reacted further without purification.

2b

17β-Cyano-15β,16β-methylene-19-nor-androsta-4,6-dien-3-one

A suspension of 3.4 g of 17β-cyano-15β,16β-methylene 3-methoxy-19-nor-androsta-3,5-diene in 100 ml of 1-methyl-2-pyrrolidone was treated in succession at 0° C. with 4 ml of a 10% strength sodium acetate solution and at this temperature with 1.6 g of 1,3-dibromo-5,5-dimethylhydantoin in portions, stirred for 0.5 hour at 0° C. (ice bath), treated with 1.5 g of lithium bromide and 1.3 g lithium carbonate, and stirred at a bath temperature of 100° C. for 3.5 hours. Subsequently, the mixture was stirred in ice water/common salt, and the precipitate was filtered off. 17β-Cyano-15β,16β(β3-methylene-19-nor-androsta-4,6-dien-3-one was obtained.

$^1$H-NMR (300 MHz, CDCl$_3$ TMS as internal standard, selected signals): δ=0.54 (m, 1H, cyclopropyl) 1.10 (m, 1H, cyclopropyl), 1.12 (s, 3H, 18-CH3), 2.80 (d, 1H, J=4.4, H-17), 5.81 (s, 1H, H-4), 6.27 (m, 1H, H-6), 6.41 (m, 1H, H-7)

EXAMPLE 3

17β-Cyano-15β,16β-methylene-7α-methyl-19-nor-androst-4-en-3-one and 17β-cyano-15β,16β-methylene-7β-methyl-19-nor-androst-4-en-3-one 67 mg of copper(I) chloride were added at room temperature to a solution of 1.0 g of 17β-cyano-15β,16β-methylene-19-nor-androsta-4,6-dien-3-one in 50 ml of tetrahydrofuran and the mixture was stirred for 10 minutes before being cooled to −15° C., treated with 450 mg of aluminium chloride, stirred at this temperature for 30 minutes, treated dropwise with 4.5 ml of methylmagnesium bromide solution (3 M in tetrahydrofuran), and stirred for one hour at −15° C. For work-up, the reaction mixture was treated at −15° C. with 30 ml of 2 M hydrochloric acid, stirred for 0.5 hours at room temperature, added to water, extracted three times with ethyl acetate, dried over sodium sulphate, concentrated in vacuo, and chromatographed on silica gel using hexane/ethyl acetate. 17β-Cyano-7α-methyl-18a-homo-19-nor-androst-4-en-3-one was obtained as fraction I and 17β-cyano-15β,16β-methylene-7β-methyl-19-nor-androst-4-en-3-one was obtained as fraction II.

17β-Cyano-15β, 16β-methylene-7α-methyl-19-nor-androst-4-en-3-one $^1$H-NMR (300 MHz, CDCl$_3$ TMS as internal standard, selected signals): δ=0.45 (m, 1H, cyclopropyl) 0.88 (d, 3H, J=6.97, 7-CH3), 1.03 (m, 1H, cyclopropyl) 1.10 (s, 3H, 18-CH3), 5.86 (s, 1H, H-4)

17β-Cyano-15β,16β-methylene-7β-methyl-9-nor-androst-4-en-3-one $^1$H-NMR (300 MHz, CDCl$_3$ TMS as internal standard, selected signals): δ=0.53 (m, 1H, cyclopropyl) 1.01 (m, 1H, cyclopropyl) 1.10 (s, 3H, 18-CH3), 1.21 (d, 3H, J=6.22, 7-CH3), 5.83 (s, 1H, H-4)

EXAMPLE 4

17β-Cyano-7α-ethyl-15β,16β-methylene-19-nor-androst-4-en-3-one and 17β-cyano-7β-ethyl-15β,16β-methylene-19-nor-androst-4-en-3-one According to the method of Example 3 using ethylmagnesium bromide in ether instead of methylmagnesium bromide, after chromatography 17β-cyano-7α-ethyl-15β,16β-methylene-19-nor-androst-4-en-3-one was obtained as fraction I and 17β-cyano-7β-ethyl-15β,16β-methylene-19-nor-androst-4-en-3-one was obtained as fraction II.

17β-Cyano-7α-ethyl-15β,16β-methylene-19-nor-androst-4-en-3-one $^1$H-NMR (300 MHz, CDCl$_3$ TMS as internal standard, selected signals): δ=0.46 (m, 1H, cyclopropyl) 0.92 (m, 3H, 7-CH3-CH2), 1.03 (m, 1H, cyclopropyl) 1.10 (s, 3H, 18-CH3), 5.87 (s, 1H, H-4)

17β-Cyano-7β-ethyl-15β,16β-methylene-19-nor-androst-4-en-3-one $^1$H-NMR (300 MHz, CDCl$_3$ TMS as internal standard, selected signals): δ=0.54 (m, 1H, cyclopropyl) 0.95 (m, 3H, 7-CH3-CH2), 1.02 (m, 1H, cyclopropyl) 1.11 (s, 3H, 18-CH3), 5.84 (s, 1H, H-4)

EXAMPLE 5

17β-Cyano-7α-vinyl-15β,16β-methylene-19-nor-androst-4-en-3-one and 17β-cyano-7β-vinyl-15β,16β-methylene-19-nor-androst-4-en-3-one According to the method of Example 3 using vinylmagnesium bromide instead of methylmagnesium bromide, after chromatography 17β-cyano-7α-vinyl-15β,16β-methylene-19-nor-androst-4-en-3-one was obtained as fraction I and 17β-cyano-7β-vinyl-15β,16β(β3-methylene-19-nor-androst-4-en-3-one was obtained as fraction II.

17β-Cyano-7α-vinyl-15β,16β-methylene-19-nor-androst-4-en-3-one $^1$H-NMR (300 MHz, CDCl$_3$ TMS as internal standard, selected signals): δ=0.51 (m, 1H, cyclopropyl), 1.08 (m, 1H, cyclopropyl) 1.14 (s, 3H, 18-CH3), 5.22 (m, 2H, CH2=CH), 5.88 (m, 1H, CH2=CH) 5.92 (s, 1H, H-4)

17β-Cyano-7β-vinyl-15β,16β-methylene-19-nor-androst-4-en-3-one $^1$H-NMR (300 MHz, CDCl$_3$ TMS as internal standard, selected signals): δ=0.42 (m, 1H, cyclopropyl), 0.95 (m, 1H, cyclopropyl) 1.10 (s, 3H, 18-CH3), 5.05 (m, 2H, CH2=CH), 5.86 (s, 1H, H-4), 5.88 (m, 1H, CH2=CH)

EXAMPLE 6

17β-Cyano-7α-cyclopropyl-15β,16β-methylene-19-nor-androst-4-en-3-one and 17β-cyano-7β-cyclopropyl-15β,16β-methylene-19-nor-androst-4-en-3-one According to the method of Example 3 using cyclopropylmagnesium bromide instead of methylmagnesium bromide, after chromatography 17β-cyano-7α-cyclopropyl-15β, 16β-methylene-19-nor-androst-4-en-3-one was obtained as fraction I and 17β-cyano-7β-cyclopropyl-15β,16β-methylene-19-nor-androst-4-en-3-one was obtained as fraction II.

17β-Cyano-7α-cyclopropyl-15β,16β-methylene-19-nor-androst-4-en-3-one $^1$H-NMR (300 MHz, CDCl$_3$ TMS as internal standard, selected signals): δ=−0.05 (m, 1H, cyclopropyl), 0.26 (m, 1H, cyclopropyl), 0.47 (m, 3H, cyclopropyl), 1.08 (s, 3H, 18-CH3), 5.90 (s, 1H, H-4)

17β-Cyano-7β-cyclopropyl-15β,16β-methylene-19-nor-androst-4-en-3-one $^1$H-NMR (300 MHz, CDCl$_3$ TMS as internal standard, selected signals): δ=0.29 (m, 2H, cyclopropyl), 0.47 (m, 1H, cyclopropyl), 0.60 (m, 2H, cyclopropyl), 0.78 (m, 1H, cyclopropyl), 0.97 (m, 3H, cyclopropyl), 1.12 (s, 3H, 18-CH3), 5.81 (s, 1H, H-4)

EXAMPLE 7

17β-Cyano-6β-hydroxymethyl-15β,16β-methylene-19-nor-androst-4-en-3-one 3 g of 17β-cyano-15β,16β-methylene-19-nor-androst-4-en-3-one (see Example 1e) were taken up in 16 ml of methanol, treated with 1.6 ml of pyrrolidine and warmed to reflux for 1 h. After cooling, the precipitate was filtered off with suction, washed with a little cold methanol and sucked dry. The crystallizate was dissolved in 30 ml of benzene and 60 ml of ethanol, and 3.1 ml of 30% strength formaldehyde solution were added. After stirring at room temperature for 2 h, the mixture was concentrated to dryness and chromatographed on silica gel. 17β-Cyano-6β-hydroxymethyl-15β,16β-methylene-19-nor-androst-4-en-3-one was obtained.

$^1$H-NMR (300 MHz, CDCl$_3$ TMS as internal standard, selected signals): δ=1.09 (s, 3H, 18-CH3), 0.43-1.06 (m, 2H, cyclopropyl), 3.74 (m, 2H, CH2OH) 5.94 (s, 1H, H-4)

EXAMPLE 8

17β-Cyano-6,6-ethylene-15β,16β-methylene-19-nor-androst-4-en-3-one

8a

17β-Cyano-15β,16β-methylene-6β-tosyloxymethyl-19-nor-androst-4-en-3-one 2.93 g of para-toluenesulphonyl chloride were added in one portion to a solution of 1.74 g of 17β-cyano-6β-hydroxymethyl-15β,16β-methylene-19-nor-androst-4-en-3-one in 20 ml of pyridine and stirred for 6 hours at room temperature. After this, the reaction mixture was poured into ice-cold 1 N HCl, and the precipitated crude product was filtered off with suction and dissolved again in ethyl acetate. After washing twice in each case with water, satd. bicarbonate solution and satd. common salt solution and drying the organic phase using sodium sulphate, after concentration to dryness 17β-cyano-15β,16β-methylene-6β-tosyloxymethyl-19-nor-androst-4-en-3-one was obtained, which was used further without purification.

8b

17β-Cyano-6,6-ethylene-15β,16β-methylene-19-nor-androst-4-en-3-one 450 mg of sodium hydride were added at room temperature in portions to a solution of 3 g of trimethylsulphoxonium iodide in 50 ml of dry DMSO and, after addition was complete, the mixture was stirred at room temperature for 1 hour. Subsequently, the solution of 1.5 g of 17β-cyano-1β55β,16β(β3-methylene-6β-tosyloxymethyl-19-nor-androst-4-en-3-one was added to the ylide formed and the mixture was stirred at room temperature for 6 hours. After termination of the reaction by the addition of 350 ml of water, extraction twice with 150 ml of ethyl acetate, washing the organic phase with water and saturated common salt solution and drying over sodium sulphate, the organic phase was concentrated, and 17β-cyano-6,6-ethylene-15β,16β-methylene-19-nor-androst-4-en-3-one was obtained.

$^1$H-NMR (300 MHz, CDCl$_3$ TMS as internal standard, selected signals): δ=0.39-1.02 (m, 6H, 6,6-ethylene/cyclopropyl) 1.11 (s, 3H, 18-CH3) 5.70 (s, 1H, H-4)

EXAMPLE 9

17β-Cyano-6β,7β-methylene-15β,16β-methylene-19-nor-androst-4-en-3-one and 17β-cyano-6α,7α-methylene-15β,16β-methylene-19-nor-androst-4-en-3-one 714 mg of sodium hydride (60% strength in paraffin) were added in portions at room temperature to a solution of 3.93 g of trimethylsulphoxonium iodide in 38 ml of dry dimethyl sulphoxide and, after addition was complete, the mixture was stirred at room temperature for 1 hour. Subsequently, the solution of 2.0 g of 17β-cyano-1β55β,16β(β3-methylene-19-nor-androsta-4,6-dien-3-one in dimethyl sulphoxide was added to the ylide formed and the mixture was stirred at room temperature for 6 hours. After termination of the reaction by addition of 150 ml of ammonium chloride solution, extraction twice with 75 ml of ethyl acetate, washing the organic phase with water and saturated common salt solution and drying over sodium sulphate, the organic phase was concentrated to dryness. After flash chromatography on silica gel using hexane/ethyl acetate and subsequent HPLC separation on a chiral stationary normal phase using an eluent of hexane and ethanol, 17β-cyano-6β,7β-methylene-1β55β,16β(β3-methylene-19-nor-androst-4-en-3-one was obtained as fraction I and 17β-cyano-6α,7α-methylene-15β,16β-methylene-19-nor-androst-4-en-3-one was obtained as fraction II.

17β-Cyano-6β,7β-methylene-15β, 16β-methylene-19-nor-androst-4-en-3-one $^1$H-NMR (300 MHz, CDCl$_3$ TMS as internal standard, selected signals): δ=0.46-0.62 (2×m, 2H, cyclopropyl) 1.06 (s, 3H, 18-CH3), 2.79 (d, 1H, J=4.14, H-17), 6.12 (s, 1H, H-4)

17β-Cyano-6α,7α-methylene-15β,16β-methylene-19-nor-androst-4-en-3-one $^1$H-NMR (300 MHz, CDCl$_3$ TMS as internal standard, selected signals): δ=0.49, 0.77, 0.83, 0.98 (4×m, 4H, cyclopropyl) 1.11 (s, 3H, 18-CH3), 2.77 (d, 1H, J=4.40, H-17), 6.05 (s, 1H, H-4)

EXAMPLE 10

17β-Cyano-17α-methyl-15β,16β-methylene-19-nor-androst-4-en-3-one

10a

17β-Cyano-17α-methyl-15β,16β-methylene 3-methoxy-19-nor-androsta-3,5-diene 14.7 ml of 2 M lithium diisopropylamide solution were added dropwise at –78° C. to a solution of 2.6 g of 17β-cyano-15β,16β-methylene 3-methoxy-19-nor-androsta-3,5-diene in 80 ml of THF. The mixture was stirred at –78° C. for 1 hour, 2.35 ml of methyl iodide were added and it was then warmed to room temperature. 25 ml of saturated ammonium chloride were added, and the mixture was extracted with three times 100 ml of ethyl acetate. The combined organic extracts were concentrated and crystallized from methanol. 17β-Cyano-17α-methyl-15β,16β-methylene 3-methoxy-19-nor-androsta-3,5-diene was obtained, which was immediately reacted further.

10b

17β-Cyano-17α-methyl-15β,16β-methylene-19-nor-androst-4-en-3-one 2 g of 17β-cyano-17α-methyl-15β,16β-methylene 3-methoxy-19-nor-androsta-3,5-diene were taken up in 50 ml of methanol, and treated with 3 ml of 1 N hydrochloric acid. After 1 hour, the mixture was neutralized with saturated sodium hydrogencarbonate solution and concentrated in vacuo, the product precipitating out. It was filtered off with suction, washed with water and recrystallized from ethyl acetate. 17β-Cyano-17α-methyl-15β,16β-methylene-19-nor-androst-4-en-3-one was obtained.

$^1$H-NMR (300 MHz, CDCl$_3$ TMS as internal standard, selected signals): δ=0.42 (m, 1H, cyclopropyl) 0.86 (m, 1H, cyclopropyl), 1.06 (m, 1H, cyclopropyl), 1.18 (s, 3H, 18-CH3), 1.37 (s, 3H, 17-CH3), 5.84 (s, 1H, H-4)

EXAMPLE 11

17β-Cyano-6β-hydroxymethyl-19-nor-androst-4-en-3-one

17β-Cyano-19-nor-androst-4-en-3-one was reacted analogously to the procedure indicated in Example 8. 17β-Cyano-6β-hydroxymethyl-19-nor-androst-4-en-3-one was obtained.

$^1$H-NMR (300 MHz, CDCl$_3$ TMS as internal standard, selected signals): δ=0.97 (s, 3H, 18-CH3), 3.66 (m, 2H, CH2OH) 5.91 (s, 1H, H-4)

EXAMPLE 12

17β-Cyano-6,6-ethylidene-19-nor-androst-4-en-3-one

17β-Cyano-6β-hydroxymethyl-19-nor-androst-4-en-3-one was reacted analogously to the procedures indicated in Examples 8a and 8b. 17β-Cyano-6,6-ethylidene-19-nor-androst-4-en-3-one was thus obtained.

$^1$H-NMR (300 MHz, CDCl$_3$ TMS as internal standard, selected signals): δ=0.41 (m, 1H), 0.54 (m, 1H), 0.68 (m, 1H), 1.01 (s, 3H, 18-CH3), 2.45 (s broad, 1H), 5.69 (s, 1H, H-4)

EXAMPLE 13

17β-Cyano-19-nor-androsta-4,6-dien-3-one

13a

17β-Cyano-3-methoxy-19-nor-androsta-3,5-diene

17β-Cyano-19-nor-androst-4-en-3-one was reacted analogously to the method indicated in procedure 2a. 17β-Cyano-3-methoxy-19-nor-androsta-3,5-diene was obtained.

¹H-NMR (d6-DMSO): 0.81 (s, 3H, 18-CH3), 3.45 (s, 3H, OCH3), 5.19 (s broad, 2H, H-4 and H-6)

13b

17β-Cyano-19-nor-androsta-4,6-dien-3-one

17β-Cyano-3-methoxy-19-nor-androsta-3,5-diene was reacted analogously to the method indicated in procedure 2b. 17β-Cyano-19-nor-androsta-4,6-dien-3-one was obtained.
¹H-NMR (d6-DMSO): 0.86 (s, 3H, 18-CH3), 2.80 (d, 1H, J=4.4, H-17), 5.69 (s, 1H, H-4), 6.18 (m, 1H, H-6), 6.24 (m, 1H, H-7)

EXAMPLE 14

17β-Cyano-6β,7β-methylene-19-nor-androst-4-en-3-one and 17β-cyano-6α,7α-methylene-19-nor-androst-4-en-3-one 17β-Cyano-19-nor-androsta-4,6-dien-3-one was reacted analogously to the method indicated in Example 9. 17β-Cyano-6β,7β-methylene-19-nor-androst-4-en-3-one and 17β-cyano-6α,7α-methylene-19-nor-androst-4-en-3-one were obtained.

17β-Cyano-6β,7β-methylene-19-nor-androst-4-en-3-one

¹H-NMR (300 MHz, CDCl₃ TMS as internal standard, selected signals): δ=0.52 (m, 1H), 0.97 (m, 1H), 0.97 (s, 3H, 18-CH3), 6.11 (s, 1H, H-4)

17β-Cyano-6β,7β-methylene-19-nor-androst-4-en-3-one

¹H-NMR (300 MHz, CDCl₃ TMS as internal standard, selected signals): δ=0.66 (m, 1H), 0.78 (m, 1H), 0.89 (m, 1H), 1.01 (s, 3H, 18-CH3), 6.03 (s, 1H, H-4)

EXAMPLE 15

17β-Cyano-7α-methyl-19-nor-androst-4-en-3-one and 17β-cyano-7β-methyl-19-nor-androst-4-en-3-one 17β-Cyano-19-nor-androsta-4,6-dien-3-one was reacted analogously to the method indicated in Example 3. 17β-Cyano-7α-methyl-19-nor-androst-4-en-3-one and 17β-cyano-7β-methyl-19-nor-androst-4-en-3-one were obtained.

17β-Cyano-7α-methyl-19-nor-androst-4-en-3-one

¹H-NMR (300 MHz, CDCl₃ TMS as internal standard, selected signals): δ=0.77 (d, 3H, 7-CH3, J=7 Hz), 1.00 (s, 3H, 18-CH3), 5.84 (s, 1H, H-4)

17β-Cyano-7β-methyl-19-nor-androst-4-en-3-one

¹H-NMR (300 MHz, CDCl₃ TMS as internal standard, selected signals): δ=0.78 (d, 3H, 7-CH3, J=7 Hz), 1.00 (s, 3H, 18-CH3), 5.85 (s, 1H, H-4)

EXAMPLE 16

17β-Cyano-7α-ethyl-19-nor-androst-4-en-3-one and 17β-cyano-7β-ethyl-19-nor-androst-4-en-3-one 17β-Cyano-19-nor-androsta-4,6-dien-3-one was reacted analogously to the method indicated in Example 3, working with ethylmagnesium bromide in diethyl ether instead of with methylmagnesium bromide. 17β-Cyano-7α-ethyl-19-nor-androst-4-en-3-one and 17β-cyano-7β-ethyl-19-nor-androst-4-en-3-one were obtained.

17β-Cyano-7α-ethyl-19-nor-androst-4-en-3-one

¹H-NMR (d6-DMSO): 0.80 (t, 3H, 7-CH2-CH3, J=7.5 Hz), 0.87 (s, 3H, 18-CH3), 5.73 (s, 1H, H-4)

17β-Cyano-7β-ethyl-19-nor-androst-4-en-3-one

¹H-NMR (300 MHz, CDCl₃ TMS as internal standard, selected signals): δ=0.88 (t, 3H, 7-CH2-CH3, J=7.5 Hz), 1.00 (s, 3H, 18-CH3), 5.82 (s, 1H, H-4)

EXAMPLE 17

17β-Cyano-7α-vinyl-19-nor-androst-4-en-3-one and 17β-cyano-7β-vinyl-19-nor-androst-4-en-3-one 17β-Cyano-19-nor-androsta-4,6-dien-3-one was reacted analogously to the method indicated in Example 3, working with vinylmagnesium bromide instead of with methylmagnesium bromide. 17β-Cyano-7α-vinyl-19-nor-androst-4-en-3-one and 17β-cyano-7β-vinyl-19-nor-androst-4-en-3-one were obtained.

17β-Cyano-7α-vinyl-19-nor-androst-4-en-3-one

¹H-NMR (300 MHz, CDCl₃ TMS as internal standard, selected signals): δ=0.99 (s, 3H, 18-CH3), 5.10 (m, 2H, CH2=CH), 5.70 (m, 1H, CH2=CH), 5.85 (s, 1H, H-4)

17β-Cyano-7β-vinyl-19-nor-androst-4-en-3-one

¹H-NMR (300 MHz, CDCl₃ TMS as internal standard, selected signals): δ=0.99 (s, 3H, 18-CH3), 4.94 (d broad, 1H, J=10 Hz, CH2=CH), 5.04 (d broad, 1H, J=17 Hz, CH2=CH), 5.71 (m, 1H, CH₂=CH), 5.84 (s, 1H, H-4)

EXAMPLE 18

17β-Cyano-7α-cyclopropyl-19-nor-androst-4-en-3-one and 17β-cyano-7β-cyclopropyl-19-nor-androst-4-en-3-one 17β-Cyano-19-nor-androsta-4,6-dien-3-one was reacted analogously to the method indicated in Example 3, working with cyclopropylmagnesium bromide instead of with methylmagnesium bromide. 17β-Cyano-7α-cyclopropyl-19-nor-androst-4-en-3-one and 17β-cyano-7β-cyclopropyl-19-nor-androst-4-en-3-one were obtained.

17β-Cyano-7α-cyclopropyl-19-nor-androst-4-en-3-one

¹H-NMR (300 MHz, CDCl₃ TMS as internal standard, selected signals): δ=−0.05 (m, 1H, cyclopropyl), 0.27 (m, 1H, cyclopropyl), 0.47 (m, 3H, cyclopropyl), 1.00 (s, 3H, 18-CH3), 5.88 (s, 1H, H-4)

17β-Cyano-7β-cyclopropyl-19-nor-androst-4-en-3-one

¹H-NMR (300 MHz, CDCl₃ TMS as internal standard, selected signals): δ=0.13 (m, 1H, cyclopropyl), 0.29 (m, 1H, cyclopropyl), 0.58 (m, 4H, cyclopropyl), 1.01 (s, 3H, 18-CH3), 5.81 (s, 1H, H-4)

EXAMPLE 19

17α-Allyl-17β-cyano-19-nor-androst-4-en-3-one

17β-Cyano-3-methoxy-19-nor-androsta-3,5-diene was reacted analogously to the methods indicated in Examples 10a (allyl bromide being used instead of methyl iodide) and 10b. 17α-Allyl-17β-cyano-19-nor-androst-4-en-3-one was obtained.

¹H-NMR (300 MHz, CDCl₃ TMS as internal standard, selected signals): δ=0.85 (m, 1H), 1.15 (s, 3H, 18-CH3), 5.22 (m, 2H, —CH═CH2), 5.84 (s, 1H, H-4), 5.92 (m, 1H, —CH═CH2)

EXAMPLE 20

17β-Cyano-17α-ethyl-19-nor-androst-4-en-3-one

17β-Cyano-3-methoxy-19-nor-androsta-3,5-diene was reacted analogously to the methods indicated in examples 10a (ethyl iodide being used instead of methyl iodide) and 10b. 17β-Cyano-17α-ethyl-19-nor-androst-4-en-3-one was obtained.

¹H-NMR (d6-DMSO): 0.97 (t, 3H, 17-CH2-CH3), 1.00 (s, 3H, 18-CH3), 5.69 (m, 1H, —CH═CH2)

EXAMPLE 21

17β-Cyano-17α-methyl-19-nor-androst-4-en-3-one

21a

17β-Cyano-17α-methyl-3-methoxy-19-nor-androsta-3,5-diene

17β-Cyano-3-methoxy-19-nor-androsta-3,5-diene was reacted analogously to the method indicated in example 10a. 17β-Cyano-17α-methyl-3-methoxy-19-nor-androsta-3,5-diene was obtained.

¹H-NMR (d6-DMSO): 0.93 (s, 3H), 1.20 (s, 3H), 3.45 (s. 3H, 3-O—CH3), 5.19 (m, 2H, H4 and H6)

21b

17β-Cyano-17α-methyl-19-nor-androst-4-en-3-one

17β-Cyano-17α-methyl-3-methoxy-19-nor-androsta-3,5-diene was reacted analogously to the method indicated in Example 10b. 17β-Cyano-17α-methyl-19-nor-androst-4-en-3-one was obtained.

¹H-NMR (d6-DMSO): 0.97 (s, 3H), 1.19 (s, 3H), 5.69 (s, 1H, H-4)

EXAMPLE 22

17β-Cyano-6β-hydroxymethyl-17α-methyl-19-nor-androst-4-en-3-one

17β-Cyano-17α-methyl-19-nor-androst-4-en-3-one was reacted analogously to the procedure indicated in Example 8. 17β-Cyano-6β-hydroxymethyl-17α-methyl-19-nor-androst-4-en-3-one was obtained.

¹H-NMR (300 MHz, CDCl₃ TMS as internal standard, selected signals): δ=1.09 (s, 3H), 1.29 (s, 3H), 3.68 (m, 2H, 6-CH2—OH), 5.91 (s, 1H, H-4)

EXAMPLE 23

17β-Cyano-6,6-ethylidene-17α-methyl-19-nor-androst-4-en-3-one

17β-Cyano-6β-hydroxymethyl-17α-methyl-19-nor-androst-4-en-3-one was reacted analogously to the procedures indicated in Examples 8a and 8b. 17β-Cyano-6,6-ethylidene-17α-methyl-19-nor-androst-4-en-3-one was obtained.

¹H-NMR (300 MHz, CDCl₃ TMS as internal standard, selected signals): δ=0.40 (m, 1H), 0.54 (m, 1H), 0.68 (m, 1H), 0.94 (m, 2H), 1.11 (s, 3H), 1.29 (s, 3H), 5.68 (s, 1H, H-4)

EXAMPLE 24

17β-Cyano-17α-methyl-19-nor-androsta-4,6-dien-3-one

17β-Cyano-3-methoxy-19-nor-androsta-3,5-diene was reacted analogously to the method indicated in Example 2b. 17β-Cyano-17α-methyl-19-nor-androsta-4,6-dien-3-one was obtained.

¹H-NMR (d6-DMSO): 1.04 (s, 3H), 1.25 (s, 3H), 5.73 (s, 1H, H-4), 6.23 (m, 1H, H-6), 6.29 (m, 1H, H-7)

EXAMPLE 25

17β-Cyano-7α,17α-bismethyl-19-nor-androst-4-en-3-one

17β-Cyano-17α-methyl-19-nor-androsta-4,6-dien-3-one was reacted analogously to the method indicated in Example 3. 17β-Cyano-7a 17α-bismethyl-19-nor-androst-4-en-3-one was obtained.

¹H-NMR (300 MHz, CDCl₃ TMS as internal standard, selected signals): δ=0.78 (d, 3H, J=7 Hz, 7-CH3), 1.11 (s, 3H), 1.31 (s, 3H), 5.84 (s, 1H, H-4)

EXAMPLE 26

17β-Cyano-17α-methyl-7α-vinyl-19-nor-androst-4-en-3-one and 17β-cyano-17α-methyl-7β-vinyl-19-nor-androst-4-en-3-one 17β-Cyano-17α-methyl-19-nor-androsta-4,6-dien-3-one was reacted analogously to the method indicated in Example 3, working with vinylmagnesium bromide instead of with methylmagnesium bromide. 17β-Cyano-17α-methyl-7α-vinyl-19-nor-androst-4-en-3-one and 17β-cyano-17α-methyl-7β-vinyl-19-nor-androst-4-en-3-one were obtained.

17β-Cyano-17α-methyl-7α-vinyl-19-nor-androst-4-en-3-one

¹H-NMR (300 MHz, CDCl₃ TMS as internal standard, selected signals): δ=1.11 (s, 3H), 1.24-1.31 (m, 8H), 5.10 (m, 2H, 7-CH═CH2), 5.70 (m, 1H, 7-CH═CH2), 5.89 (s, 1H, H-4)

17β-Cyano-17α-methyl-7β-vinyl-19-nor-androst-4-en-3-one

¹H-NMR (300 MHz, CDCl₃ TMS as internal standard, selected signals): δ=1.09 (s, 3H), 1.26 (s, 3H), 4.93 (d broad, 1H, J=10 Hz, 7-CH=CH2), 5.03 (d broad, 1H, J=17 Hz, 7-CH=CH2), 5.71 (m, 1H, 7-CH=CH2), 5.83 (s, 1H, H-4)

EXAMPLE 27

17β-Cyano-7α-cyclopropyl-17α-methyl-19-nor-androst-4-en-3-one and 17β-cyano-7β-cyclopropyl-17α-methyl-19-nor-androst-4-en-3-one 17β-Cyano-17α-methyl-19-nor-androsta-4,6-dien-3-one was reacted analogously to the method indicated in Example 3, working with cyclopropylmagnesium bromide instead of with methylmagnesium bromide. 17β-Cyano-7α-cyclopropyl-17α-methyl-19-nor-androst-4-en-3-one and 17β-cyano-7β-cyclopropyl-17α-methyl-19-nor-androst-4-en-3-one were obtained.

17β-Cyano-7α-cyclopropyl-17α-methyl-19-nor-androst-4-en-3-one $^1$H-NMR (300 MHz, CDCl$_3$ TMS as internal standard, selected signals): δ=−0.05 (m, 1H), 0.26 (m, 1H), 0.39-0.58 (m, 3H), 1.10 (s, 3H), 1.32 (s, 3H), 5.89 (s, 1H, H-4) 17β-Cyano-7β-cyclopropyl-17α-methyl-19-nor-androst-4-en-3-one:

$^1$H-NMR (300 MHz, CDCl$_3$ TMS as internal standard, selected signals): δ=0.12 (m, 1H), 0.30 (m, 1H), 0.59 (m, 4H), 0.87 (m, 1H), 1.12 (s, 3H), 1.30 (s, 3H), 5.81 (s, 1H, H-4)

EXAMPLE 28

17β-Cyano-17α-methyl-15β,16β-methylene-19-nor-androsta-4,6-dien-3-one

A suspension of 3.4 g of 17β-cyano-17α-methyl-15β,16β-methylene 3-methoxy-19-nor-androsta-3,5-diene in 100 ml of 1-methyl-2-pyrrolidone was treated successively at 0° C. with 4 ml of a 10% strength sodium acetate solution and at this temperature with 1.6 g of 1,3-dibromo-5,5-dimethylhydantoin in portions, stirred at 0° C. for 0.5 hour (ice bath), treated with 1.5 g of lithium bromide and 1.3 g of lithium carbonate, and stirred for 3.5 hours at a bath temperature of 100° C. Subsequently, it was stirred into a mixture of ice water and common salt solution, the precipitate was filtered off and the filter cake was recrystallized from dimethoxyethane. 17β-Cyano-17α-methyl-15β,16β-methylene-19-nor-androsta-4,6-dien-3-one was obtained.

17β-Cyano-17α-methyl-15β,16β-methylene-19-nor-androsta-4,6-dien-3-one $^1$H-NMR (300 MHz, CDCl$_3$ as internal standard, selected signals): δ=0.55 (m, 1H, cyclopropyl) 1.18 (m, 1H, cyclopropyl), 1.25 (s, 3H, 18-CH2), 1.44 (s, 3H, 17-CH2), 5.85 (s, 1H, H-4), 6.29 (m, 1H, H-6), 6.45 (m, 1H, H-7)

EXAMPLE 29

17β-Cyano-17α-ethyl-15β,16β-methylene-19-nor-androst-4-en-3-one

29a

17β-Cyano-17α-ethyl-15β,16β-methylene 3-methoxy-19-nor-androsta-3,5-diene

17β-Cyano-15β,16β-methylene 3-methoxy-19-nor-androsta-3,5-diene was reacted as described in Example 10a. Instead of the methyl iodide employed there, ethyl iodide was used here. 17β-Cyano-17α-ethyl-15β,16β-methylene 3-methoxy-19-nor-androsta-3,5-diene was obtained.

29b

17β-Cyano-17α-ethyl-15β,16β-methylene-19-nor-androst-4-en-3-one

The compound described in Example 19a was reacted analogously to the procedure indicated in Example 10b. 17β-Cyano-17α-ethyl-15β,16β-methylene-19-nor-androst-4-en-3-one was obtained.

17β-Cyano-17α-ethyl-15β,16β-methylene-19-nor-androst-4-en-3-one $^1$H-NMR (CDCl3): 0.46 (m, 1H, cyclopropyl) 0.87 (m, 1H, cyclopropyl), 1.08 (m, 1H, cyclopropyl), 1.21 (m, 7H, 18-CH2, 17-CH2-CH2 cyclopropyl), 5.86 (s, 1H, H-4)

EXAMPLE 30

17β-Cyano-17α-ethyl-6β-hydroxymethyl-15β,16β-methylene-19-nor-androst-4-en-3-one 17β-Cyano-17α-ethyl-15β,16β-methylene-19-nor-androst-4-en-3-one was reacted analogously to Example 7, and 17β-cyano-17α-ethyl-6β-hydroxymethyl-15β,16β-methylene-19-nor-androst-4-en-3-one was obtained.

17β-Cyano-17α-ethyl-6β-hydroxymethyl-15β,16β-methylene-19-nor-androst-4-en-3-one $^1$H-NMR (CDCl3): 0.46 (m, 1H, cyclopropyl), 1.19 (m, 6H, 17-CH$_2$—CH3, 18-CH3), 3.74 (m, 2H, CH2OH) 5.94 (s, 1H, H-4)

EXAMPLE 31

17β-Cyano-17α-ethyl-6,6-ethylene-15β,16β-methylene-19-nor-androst-4-en-3-one

17β-Cyano-17α-ethyl-6β-hydroxymethyl-15β,16β-methylene-19-nor-androst-4-en-3-one was reacted analogously to Example 8, 17β-cyano-17α-ethyl-6,6-ethylene-15β,16β-methylene-19-nor-androst-4-en-3-one was obtained.

17β-Cyano-17α-ethyl-6,6-ethylene-15β,16β-methylene-19-nor-androst-4-en-3-one $^1$H-NMR (CDCl3): 0.43 (m, 2H, 6,6-ethylene/cyclopropyl), 0.59, 0.79, 0.96, 1.08 (4×m, 4H, 6,6-ethylene), 1.22 (m, 6H, 17-CH2-CH3β, 18-CH3) 5.70 (s, 1H, H-4)

EXAMPLE 32

17β-Cyano-17α-ethyl-15β,16β-methylene-19-nor-androsta-4,6-dien-3-one

From 17β-cyano-17α-ethyl-15β,16β-methylene 3-methoxy-19-nor-androsta-3,5-diene,
17β-cyano-17α-ethyl-15β,16β-methylene-19-nor-androsta-4,6-dien-3-one was obtained analogously to the procedure indicated in Example 2b.
17β-Cyano-17α-ethyl-15β,16β-methylene-19-nor-androsta-4,6-dien-3-one:

¹H-NMR (CDCl3): 0.53 (m, 1H, cyclopropyl) 1.09-1.28 (m, 9H, 18-CH3, 17-CH2-CH3 cyclopropyl), 5.80 (s, 1H, H-4), 6.25 (m, 1H, H-6), 6.40 (m, 1H, H-7)

EXAMPLE 33

17β-Cyano-17α-ethyl-7α-methyl-15β,16β-methylene-19-nor-androst-4-en-3-one and 17β-cyano-17α-ethyl-7β-methyl 15β,16β-methylene-19-nor-androst-4-en-3-one 17β-Cyano-17α-ethyl-15β,16β-methylene-19-nor-androsta-4,6-dien-3-one was reacted analogously to Example 3, and after chromatography, 17β-cyano-17α-ethyl-7α-methyl-15β,16β-methylene-19-nor-androst-4-en-3-one was obtained as fraction 1 and 17β-cyano-17α-ethyl-7β-methyl 15β,16β-methylene-19-nor-androst-4-en-3-one was obtained as fraction II.

17β-Cyano-17α-ethyl-7α-methyl-15β,16β-methylene-19-nor-androst-4-en-3-one

¹H-NMR (CDCl3): 0.45 (m, 1H, cyclopropyl), 0.87 (d, 3H, J=7.34, 7-CH3), 1.23 (m, 6H, 18-CH3, 17-CH2-CH3), 5.86 (s, 1H, H-4)

17β-Cyano-17α-ethyl-7β-methyl 15β,16β-methylene-19-nor-androst-4-en-3-one

¹H-NMR (CDCl3): 0.53 (m, 1H, cyclopropyl), 1.22 (m, 9H, 7-CH3, 18-CH3, 17-CH2-CH3), 5.82 (s, 1H, H-4)

EXAMPLE 34

17β-Cyano-17α,7α-diethyl-15β,16β-methylene-19-nor-androst-4-en-3-one and 17β-cyano-17α,7β-diethyl-15β,16β-methylene-19-nor-androst-4-en-3-one According to the method of Example 3 using ethylmagnesium bromide in ether instead of methylmagnesium bromide, from 17β-cyano-17α-ethyl-15β,16β-methylene-19-nor-androsta-4,6-dien-3-one, after chromatography, 17β-cyano-17α,7α-diethyl-15β,16β-methylene-19-nor-androst-4-en-3-one was obtained as fraction I and 17β-cyano-17α,7β-diethyl-15β,16β-methylene-19-nor-androst-4-en-3-one was obtained as fraction II.

17β-Cyano-17α,7α-diethyl-15β,16β-methylene-19-nor-androst-4-en-3-one

¹H-NMR (CDCl3): 0.46 (m, 1H, cyclopropyl) 0.92 (t, 3H, J=7.34, 7-CH2-CH3), 1.23 (m, 6H, 18-CH3, 17-CH2-CH3), 5.87 (s, 1H, H-4)

17β-Cyano-17α,7β-diethyl-15β,16β-methylene-19-nor-androst-4-en-3-one

¹H-NMR (CDCl3): 0.54 (m, 1H, cyclopropyl) 0.94 (t, 3H, J=7.34, 7-CH2-CH3), 1.21 (t, 3H, J=7.34, 17-CH2-CH3) 1.24 (s, 3H, 18-CH3), 5.84 (s, 1H, H-4)

EXAMPLE 35

17β-Cyano-17α-ethyl-7α-vinyl-15β,16β-methylene-19-nor-androst-4-en-3-one and 17β-cyano-17α-ethyl-7β-vinyl-15β,16β-methylene-19-nor-androst-4-en-3-one According to the method of Example 3 using vinylmagnesium bromide instead of methylmagnesium bromide, from 17β-cyano-17α-ethyl-15β,16β-methylene-19-nor-androsta-4,6-dien-3-one, after chromatography, 17β-cyano-17α-ethyl-7α-vinyl-15β,16β-methylene-19-nor-androst-4-en-3-one is obtained as fraction I and 17β-cyano-17α-ethyl-7β-vinyl-15β,16β-methylene-19-nor-androst-4-en-3-one is obtained as fraction II.

17β-Cyano-17α-ethyl-7α-vinyl-15β,16β-methylene-19-nor-androst-4-en-3-one

¹H-NMR (CDCl3): 0.46 (m, 1H, cyclopropyl), 1.08 (m, 1H, cyclopropyl) 1.22 (m, 3H, CH2-CH3), 1.27 (s, 3H, 18-CH3), 5.17 (m, 2H, CH2=CH), 5.81 (m, 1H, CH2=CH) 5.87 (s, 1H, H-4)

17β-Cyano-17α-ethyl-7β-vinyl-15β,16β-methylene-19-nor-androst-4-en-3-one

¹H-NMR (CDCl3): 0.42 (m, 1H, cyclopropyl), 0.99 (m, 1H, cyclopropyl) 1.24 (m, 6H, 18-CH3, CH2-CH3), 5.02 (m, 2H, CH2=CH), 5.85 (s, 1H, H-4), 5.90 (m, 1H, CH2=CH)

EXAMPLE 36

17β-Cyano-17α-ethyl-7α-cyclopropyl-15β,16β-methylene-19-nor-androst-4-en-3-one and 17β-cyano-17α-ethyl-7β-cyclopropyl-15β,16β-methylene-19-nor-androst-4-en-3-one According to the method of Example 3 using cyclopropylmagnesium bromide instead of methylmagnesium bromide, from 17β-cyano-17α-ethyl-15β,16β-methylene-19-nor-androsta-4,6-dien-3-one, after chromatography, 17β-cyano-17α-ethyl-7α-cyclopropyl-15β,16β-methylene-19-nor-androst-4-en-3-one is obtained as fraction I and 17β-cyano-17α-ethyl-7β-cyclopropyl-15β,16β-methylene-19-nor-androst-4-en-3-one is obtained as fraction II.

17β-Cyano-17β-ethyl-7α-cyclopropyl-15β,16β-methylene-19-nor-androst-4-en-3-one

¹H-NMR (CDCl3): −0.05 (m, 1H, cyclopropyl), 0.26 (m, 1H, cyclopropyl), 0.42 (m, 3H, cyclopropyl), 1.22 (m, 6H, CH2-CH3, 18-CH3), 5.90 (s, 1H, H-4)

17β-Cyano-17β-ethyl-7β-cyclopropyl-15β,16β-methylene-19-nor-androst-4-en-3-one

¹H-NMR (CDCl3): 0.25 (m, 1H, cyclopropyl), 0.33 (m, 1H, cyclopropyl), 0.47 (m, 1H, cyclopropyl), 0.60 (m, 2H, cyclopropyl), 1.06 (m, 1H, cyclopropyl), 1.22 (m, 3H, CH2-CH3), 1.27 (s, 3H, 18-CH3), 5.81 (s, 1H, H-4)

EXAMPLE 37

17β-Cyano-17α-ethyl-6β,7β-methylene-15β,16β-methylene-19-nor-androst-4-en-3-one and 17β-cyano-17α-ethyl-6α,7α-methylene-15β,16β-methylene-19-nor-androst-4-en-3-one 17β-Cyano-17α-ethyl-15β,16β-methylene-19-nor-androsta-4,6-dien-3-one is reacted according to the method indicated in Example 9 and, after chromatography, 17β-cyano-17α-ethyl-6β,7β-methylene-15β,16β-methylene-19-nor-androst-4-en-3-one is obtained as fraction I and 17β- cyano-17α-ethyl-6α,7α-methylene-15β,16β-methylene-19-nor-androst-4-en-3-one is obtained as fraction II.

17β-Cyano-17α-ethyl-6β,7β-methylene-15β,16β-methylene-19-nor-androst-4-en-3-one

¹H-NMR (CDCl₃): 0.49 (m, 1H, cyclopropyl), 0.78 (m, 2H, cyclopropyl), 0.96 (m, 1H, cyclopropyl), 1.13 (m, 1H, cyclopropyl), 1.23 (m, 6H, CH2-CH3, 18-CH3), 6.05 (s, 1H, H-4)

17β-Cyano-17α-ethyl-6α,7α-methylene-15β,16β-methylene-19-nor-androst-4-en-3-one

¹H-NMR (CDCl₃): 0.52 (m, 1H, cyclopropyl), 0.59 (m, 1H, cyclopropyl), 0.97 (m, 1H, cyclopropyl), 1.17 (m, 1H, cyclopropyl), 1.18 (s, 3H, 18-CH3), 1.23 (m, 3H, CH2-CH3), 6.12 (s, 1H, H-4)

EXAMPLE 38

17β-Cyano-17α,7α-dimethyl-15β,16β-methylene-19-nor-androst-4-en-3-one and 17β-cyano-17α,7β-dimethyl 15β,16β-methylene-19-nor-androst-4-en-3-one 17β-Cyano-17α-methyl-15β,16β(β3-methylene-19-nor-androsta-4,6-dien-3-one is reacted analogously to Example 3, and, after chromatography, 17β-cyano-17α,7α-dimethyl-1β (5β,16β(β3-methylene-19-nor-androst-4-en-3-one is obtained as fraction I and 17β-cyano-17α,7β-dimethyl 15β,16β-methylene-19-nor-androst-4-en-3-one is obtained as fraction II.

17β-Cyano-17α,7α-dimethyl-15β,16β-methylene-19-nor-androst-4-en-3-one

¹H-NMR (CDCl3): 0.44 (m, 1H, cyclopropyl) 0.88 (d, 3H, J=6.97 Hz, 7-CH3), 1.08 (m, 1H, cyclopropyl) 1.20 (s, 3H, 18-CH3), 1.40 (s, 3H, 17-CH3), 5.86 (s, 1H, H-4)

17β-Cyano-17α,7β-dimethyl-15β,16β-methylene-19-nor-androst-4-en-3-one

¹H-NMR (CDCl3): 0.51 (m, 1H, cyclopropyl), 0.98 (m, 1H, cyclopropyl), 1.06 (m, 1H, cyclopropyl), 1.20 (s, 3H, 18-CH3), 1.22 (d, 3H, J=5.87 Hz, 7-CH3), 1.38 (s, 3H, 17-CH3), 5.83 (s, 1H, H-4)

EXAMPLE 39

17β-Cyano-17α-methyl-7α-ethyl-15β,16β-methylene-19-nor-androst-4-en-3-one and 17β-cyano-17α-methyl-7β-ethyl-15β,16β-methylene-19-nor-androst-4-en-3-one 17β-Cyano-17α-methyl-15β, 16β-methylene-19-nor-androsta-4,6-dien-3-one is reacted according to the method of Example 3 using ethylmagnesium bromide in ether instead of methylmagnesium bromide, and, after chromatography, 17β-cyano-17α-methyl-7α-ethyl-15β,16β-methylene-19-nor-androst-4-en-3-one is obtained as fraction I and 17β-cyano-17α-methyl-7β-ethyl-15β,16β-methylene-19-nor-androst-4-en-3-one is obtained as fraction II.

17β-Cyano-17α-methyl-7α-ethyl-15β,16β-methylene-19-nor-androst-4-en-3-one

¹H-NMR (CDCl3): 0.45 (m, 1H, cyclopropyl) 0.92 (m, 3H, 7-CH3-CH2), 1.20 (s, 3H, 18-CH3), 1.39 (s, 3H, 17-CH3), 5.87 (s, 1H, H-4)

17β-Cyano-17α-methyl-7β-ethyl-15β,16β-methylene-19-nor-androst-4-en-3-one

¹H-NMR (CDCl3): 0.52 (m, 1H, cyclopropyl) 0.94 (m, 3H, 7-CH2-CH3), 1.07 (m, 1H, cyclopropyl) 1.21 (s, 3H, 18-CH3), 1.38 (s, 3H, 17-CH3), 5.84 (s, 1H, H-4)

EXAMPLE 40

17β-Cyano-17α-methyl-7α-vinyl-15β,16β-methylene-19-nor-androst-4-en-3-one and 17β-cyano-17α-methyl-7β-vinyl-15β,16β-methylene-19-nor-androst-4-en-3-one 17β-Cyano-17α-methyl-15β,16β-methylene-19-nor-androsta-4,6-dien-3-one is reacted according to the method of Example 3 using vinylmagnesium bromide instead of methylmagnesium bromide, and, after chromatography, 17β-cyano-17α-methyl-7α-vinyl-15β,16β-methylene-19-nor-androst-4-en-3-one is obtained as fraction I and 17β-cyano-17α-methyl-7β-vinyl-15β,16β-methylene-19-nor-androst-4-en-3-one is obtained as fraction II.

17β-Cyano-17α-methyl-7α-vinyl-15β,16β-methylene-19-nor-androst-4-en-3-one

¹H-NMR (CDCl3): 0.45 (m, 1H, cyclopropyl), 1.09 (m, 1H, cyclopropyl) 1.19 (s, 3H, 18-CH3), 1.37 (s, 3H, 17-CH3), 5.16 (m, 2H, CH2=CH), 5.82 (m, 1H, CH2=CH) 5.87 (s, 1H, H-4)

17β-Cyano-17α-methyl-7β-vinyl-15β,16β-methylene-19-nor-androst-4-en-3-one

¹H-NMR (CDCl3): 0.40 (m, 1H, cyclopropyl), 0.98 (m, 2H, cyclopropyl) 1.20 (s, 3H, 18-CH3), 1.36 (s, 3H, 17-CH3), 5.03 (m, 2H, CH2=CH), 5.85 (s, 1H, H-4), 5.90 (m, 1H, CH2=CH)

EXAMPLE 41

17β-Cyano-17α-methyl-7α-cyclopropyl-15β,16β-methylene-19-nor-androst-4-en-3-one and 17β-cyano-17α-methyl-7β-cyclopropyl-15β,16β-methylene-19-nor-androst-4-en-3-one 17β-Cyano-17α-methyl-15β,16β-methylene-19-nor-androsta-4,6-dien-3-one is reacted according to the method of Example 3 using cyclopropylmagnesium bromide instead of methylmagnesium bromide, and, after chromatography, 17β-cyano-17α-methyl-7α-cyclopropyl-15β,16β-methylene-19-nor-androst-4-en-3-one is obtained as fraction I and 17β-cyano-17α-methyl-7β-cyclopropyl-15β,16β-methylene-19-nor-androst-4-en-3-one is obtained as fraction II.

17β-Cyano-17α-methyl-7α-cyclopropyl-15β,16β-methylene-19-nor-androst-4-en-3-one

¹H-NMR (CDCl3): 0.05 (m, 1H, cyclopropyl), 0.35 (m, 1H, cyclopropyl), 0.41 (m, 1H, cyclopropyl), 0.49 (m, 1H, cyclopropyl), 0.59 (m, 2H, cyclopropyl), 1.19 (s, 3H, 18-CH3), 1.41 (s, 3H, 17-CH3), 5.90 (s, 1H, H-4)

17β-Cyano-17α-methyl-7β-cyclopropyl-15β,16β-methylene-19-nor-androst-4-en-3-one $^1$H-NMR (CDCl3): 0.25 (m, 1H, cyclopropyl), 0.33 (m, 1H, cyclopropyl), 0.45 (m, 1H, cyclopropyl), 0.60 (m, 2H, cyclopropyl), 0.79 (m, 1H, cyclopropyl), 0.87 (m, 1H, cyclopropyl), 0.94 (m, 1H, cyclopropyl), 1.07 (m, 1H, cyclopropyl), 1.22 (s, 3H, 18-CH3), 1.39 (s, 3H, 17-CH3), 5.82 (s, 1H, H-4)

EXAMPLE 42

17β-Cyano-17α-methyl-6β-hydroxymethyl-15β,16β-methylene-19-nor-androst-4-en-3-one 17β-Cyano-17α-methyl-15β,16β-methylene-19-nor-androst-4-en-3-one is reacted analogously to the process indicated in Example 7. 17β-Cyano-17α-methyl-6β-hydroxymethyl-15β,16β-methylene-19-nor-androst-4-en-3-one is obtained.

17β-Cyano-17α-methyl-6β-hydroxymethyl-15β,16β-methylene-19-nor-androst-4-en-3-one $^1$H-NMR (CDCl3): 0.45 (m, 1H, cyclopropyl), 1.08 (m, 1H, cyclopropyl), 1.18 (s, 3H, 18-CH3), 1.38 (s, 3H, 17-CH3), 3.74 (m, 2H, CH2OH) 5.94 (s, 1H, H-4)

EXAMPLE 43

17β-Cyano-17α-methyl-6,6-ethylene-15β,16β-methylene-19-nor-androst-4-en-3-one

17β-Cyano-17α-methyl-6β-hydroxymethyl-15β,16β-methylene-19-nor-androst-4-en-3-one is reacted analogously to the process indicated in Examples 8a and 8b. 17β-Cyano-17α-methyl-6,6-ethylene-15β,16β-methylene-19-nor-androst-4-en-3-one is obtained.

17β-Cyano-17α-methyl-6,6-ethylene-15β,16β-methylene-19-nor-androst-4-en-3-one $^1$H-NMR (CDCl3): 0.42-1.08 (m, 6H, 6,6-ethylene/cyclopropyl) 1.22 (s, 3H, 18-CH3), 1.39 (s, 3H, 17-CH3), 5.70 (s, 1H, H-4)

EXAMPLE 44

17β-Cyano-17α-methyl-6β,7β-methylene-15β,16β-methylene-19-nor-androst-4-en-3-one and 17β-cyano-17α-methyl-6α,7α-methylene-15β,16β-methylene-19-nor-androst-4-en-3-one 17β-Cyano-17α-methyl-15β,16β-methylene-19-nor-androsta-4,6-dien-3-one is reacted analogously to the method indicated in Example 9 and 17β-cyano-17α-methyl-6β,7β-methylene-15β,16β-methylene-19-nor-androst-4-en-3-one is obtained as fraction I and 17β-cyano-17α-methyl-6α,7α-methylene-15β,16β-methylene-19-nor-androst-4-en-3-one is obtained as fraction II.

17β-Cyano-17α-methyl-6β,7β-methylene-15β,16β-methylene-19-nor-androst-4-en-3-one $^1$H-NMR (CDCl$_3$): 0.47 (m, 1H, cyclopropyl), 0.80 (m, 2H, cyclopropyl), 0.97 (m, 1H, cyclopropyl), 1.13 (m, 1H, cyclopropyl), 1.22 (s, 3H, 18-CH3), 1.40 (s, 3H, 17-CH3), 6.05 (s, 1H, H-4)

17β-Cyano-17α-methyl-6α,7α-methylene-15β,16β-methylene-19-nor-androst-4-en-3-one $^1$H-NMR (CDCl$_3$): 0.50 (m, 1H, cyclopropyl), 0.59 (m, 1H, cyclopropyl), 0.98 (m, 1H, cyclopropyl), 1.16 (s, 3H, 18-CH3), 1.41 (s, 3H, 17-CH3), 6.12 (s, 1H, H-4)

EXAMPLE 45

17β-Cyano-17α-methyl-6β,7β-methylene-19-nor-androst-4-en-3-one and 17β-cyano-17α-methyl-6α,7α-methylene-19-nor-androst-4-en-3-one 17β-Cyano-17α-methyl-19-nor-androsta-4,6-dien-3-one is reacted according to the method indicated in Example 9 and, after chromatography, 17β-cyano-17α-methyl-6β,7α-methylene-19-nor-androst-4-en-3-one is obtained as fraction I and 17β-cyano-17α-methyl-6β,7β-methylene-19-nor-androst-4-en-3-one is obtained as fraction II.

17β-Cyano-17α-methyl-6α,7α-methylene-19-nor-androst-4-en-3-one $^1$H-NMR (CDCl$_3$): 0.68 (m, 1H), 0.77 (m, 1H), 0.90 (m, 1H), 1.12 (s, 3H, CH$_3$), 1.32 (s, 3H, CH$_3$), 1.68 (m, 1H), 2.02 (m, 1H), 2.17 (m, 1H), 2.40 (m, 1H), 2.51 (m, 1H), 6.03 (s, 1H, H-4)

17β-Cyano-17α-methyl-6β,7β-methylene-19-nor-androst-4-en-3-one $^1$H-NMR (CDCl$_3$): 0.52 (m, 1H), 0.93 (m, 1H), 1.08 (s, 3H, CH$_3$), 1.33 (s, 3H, CH$_3$), 1.95 (m, 1H), 2.37-2.48 (m, 2H), 6.11 (s, 1H, H-4)

EXAMPLE 46

4-Chloro-17β-cyano-17α-ethyl-19-nor-androst-4-en-3-one 100 mg of 17β-cyano-17α-ethyl-19-nor-androst-4-en-3-one are dissolved in 1.1 ml of pyridine and cooled to 0° C. After addition of 42 µl of sulfuryl chloride, the mixture is subsequently stirred at 0° C. for 1.5 hours.

After admixing with saturated aqueous sodium bicarbonate solution, water and ethyl acetate, the phases are separated and the organic phase is washed with water and saturated aqueous sodium chloride solution. After drying of the organic phase over sodium sulfate and filtration, the filtrate is concentrated and the residue is chromatographed on silica gel using a mixture of ethyl acetate and n-hexane to obtain 4-chloro-17β-cyano-17α-ethyl-19-nor-androst-4-en-3-one.

4-Chloro-17β-cyano-17α-ethyl-19-nor-androst-4-en-3-one $^1$H-NMR (d6-DMSO): 0.97 (t, 3H, J=7.3, —CH$_2$—CH$_3$), 1.00 (s, 3H, —CH$_3$), 1.99 (m, 1H), 2.08-2.22 (m, 2H), 3.10 (m, 1H)

EXAMPLE 47

17β-Cyano-3-hydroxyimino-17α-ethyl-19-nor-androst-4-en-3-one 100 mg of 17β-cyano-17α-ethyl-19-nor-androst-4-en-3-one are dissolved in 1 ml of pyridine and admixed with 34.5 mg of hydroxylamine hydrochloride. After one hour's stirring at 125° C. bath temperature, the batch is partitioned between water and ethyl acetate. The organic phase is washed with water and saturated aqueous sodium chloride solution, dried over sodium sulfate and filtered, and the filtrate is concentrated. After chromatography on silica gel using a mixture of ethyl acetate and n-hexane, the product-containing eluate is concentrated and recrystallized from a mixture of acetone and diisopropyl ether to obtain 17β-cyano-3-hydroxyimino-17α-ethyl-19-nor-androst-4-en-3-one as E/Z mixture of the oximes.

17β-Cyano-3-hydroxyimino-17α-ethyl-19-nor-androst-4-en-3-one $^1$H-NMR (d6-DMSO): 0.41 (m, 1H), 0.96 (t, 3H, J=7.3, —CH$_2$—CH$_3$), 0.99 (s, 3H, —CH$_3$), 2.82 and 2.98 (each m, together 1H), 5.76 and 6.36 (each s, together 1H, H-4)

EXAMPLE 48

17β-Cyano-19-nor-androsta-4,9-dien-3-one

48a

17β-Cyano-3,3-dimethoxyestr-5(10)-ene 75 g of 3,3-dimethoxyestr-5(10)-en-17-one are reacted analogously to the method indicated in Example 1d. The crude product thus obtained is taken up in a mixture of diisopropyl ether and hexane, the residue is filtered off and the filtrate is concentrated. The evaporation residue is crystallized from diisopropyl ether to obtain 17β-cyano-3,3-dimethoxyestr-5(1β10)-ene.

17β-Cyano-3,3-dimethoxyestr-5(10)-ene $^1$H-NMR (d6-DMSO): 0.84 (s, 3H, 17-CH$_3$), 1.46 (m, 1H), 1.70 (m, 1H), 2.57 (m, 1H), 3.07 (s, 3H, 3-OCH$_3$), 3.10 (s, 3H, 3-OCH$_3$)

48b

17β-Cyanoestr-5(10)-en-3-one 3 g of 17β-cyano-3,3-dimethoxyestr-5(10)-ene are suspended in a mixture of 24 ml of dichloromethane and 70 ml of t-butanol. After addition of 28 ml of water and 0.11 ml of 60% perchloric acid, the batch is stirred until fully reacted, admixed with saturated aqueous sodium bicarbonate and extracted with ethyl acetate. The organic phase is washed with saturated aqueous sodium chloride solution, dried over sodium sulfate and filtered and the filtrate is evaporated to dryness to leave 17β-cyanoestr-5(10)-en-3-one which is further processed without purification.

48c

17β-Cyano-19-nor-androsta-4,9-dien-3-one 2.4 g of 17β-cyanoestr-5(1β10)-en-3-one are admixed with 35 ml of pyridine and 3.2 g of pyridinium hydrobromide-perbromide. The mixture is stirred at room temperature for 1 hour and then at 50° C. for 4 hours. After cooling, 40 ml of ice-cold 6N aqueous hydrochloric acid are added and the mixture is extracted with ethyl acetate. The organic phase is washed with 1N aqueous hydrochloric acid and saturated aqueous sodium bicarbonate solution, dried over sodium sulfate and filtered, and the filtrate evaporation residue is purified by means of chromatography on silica gel using a mixture of ethyl acetate and n-hexane to obtain 17β-cyano-19-nor-androsta-4,9-dien-3-one.

17β-Cyano-19-nor-androsta-4,9-dien-3-one $^1$H-NMR (d6-DMSO): 0.94 (s, 3H, 17-CH$_3$), 1.09-1.22 (m, 2H), 1.25-1.41 (m, 2H), 1.69 (m, 1H), 2.59 (m, 1H), 2.75-2.90 (m, 2H), 5.56 (s, 1H, H-4)

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 10 2007 027 637.2, filed Jun. 12, 2007 and U.S. Provisional Application Ser. No. 60/943,617, filed Jun. 13, 2007, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A 17β-Cyano-19-nor-androst-4-ene derivative that is
    17β-cyano-15β,16β-methylene-19-nor-androst-4-en-3-one,
    17β-cyano-17α-methyl-15β,16β-methylene-19-nor-androst-4-en-3-one,
    17β-cyano-17α-ethyl-15β,16β-methylene-19-nor-androst-4-en-3-one,
    17β-cyano-15β,16β-methylene-19-nor-androsta-4,6-dien-3-one,
    17β-cyano-7α-methyl-15β,16β-methylene-19-nor-androsta-4-en-3-one,
    17β-cyano-17α-methyl-15β,16β-methylene-19-nor-androsta-4,6-dien-3-one,
    or
    17β-cyano-17α-ethyl-6β,7β-methylene-15β,16β-methylene-19-nor-androst-4-en-3-one.

2. A method for oral contraception or for the treatment of pre-, peri- or postmenopausal symptoms, comprising administering to a subject in need thereof an effective amount of a compound according to claim 1.

3. A method according to claim 2, wherein the medicament has gestagenic and antimineralcorticoid action.

4. A pharmaceutical composition comprising at least one 17β-cyano-19-nor-androst-4-ene derivative according to claim 1 and at least one suitable pharmaceutically acceptable carrier.

5. The composition according to claim 4, further comprising at least one oestrogen.

6. The composition according to claim 5, wherein the oestrogen is ethinylestradiol.

7. The composition according to claim 5, wherein the oestrogen is a natural oestrogen.

8. The composition according to claim 7, wherein the natural oestrogen is oestradiol.

9. The composition according to claim 7, wherein the natural oestrogen is oestradiol valerate.

10. The composition according to claim 7, wherein the natural oestrogen is a conjugated oestrogen.

* * * * *